(12) United States Patent
Ashrafi et al.

(10) Patent No.: US 10,197,554 B2
(45) Date of Patent: *Feb. 5, 2019

(54) SYSTEM AND METHOD FOR EARLY DETECTION OF ALZHEIMERS BY DETECTING AMYLOID-BETA USING ORBITAL ANGULAR MOMENTUM

(71) Applicants: NxGen Partners IP, LLC, Dallas, TX (US); Nita Sue Linquist, Dallas, TX (US)

(72) Inventors: Solyman Ashrafi, Plano, TX (US); Roger Linquist, Dallas, TX (US)

(73) Assignee: NxGen Partners IP, LLP, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/729,087

(22) Filed: Oct. 10, 2017

(65) Prior Publication Data

US 2018/0031538 A1 Feb. 1, 2018

Related U.S. Application Data

(63) Continuation of application No. 14/875,507, filed on Oct. 5, 2015, now Pat. No. 9,784,724, which is a (Continued)

(51) Int. Cl.
*G01N 33/48* (2006.01)
*G01N 33/487* (2006.01)
*G01N 33/68* (2006.01)

(52) U.S. Cl.
CPC ....... *G01N 33/487* (2013.01); *G01N 33/6896* (2013.01); *G01N 2333/4709* (2013.01); *G01N 2800/2821* (2013.01)

(58) Field of Classification Search
CPC ....... G01N 33/6896; G01N 2800/2821; G01N 2800/52; G01N 21/17; G01N 21/21;
(Continued)

(56) References Cited

U.S. PATENT DOCUMENTS 3,459,466 A 8/1969 Giordmaine
3,614,722 A 10/1971 Jones
(Continued)

FOREIGN PATENT DOCUMENTS

WO 2013092764 A1 6/2013

OTHER PUBLICATIONS

Solyman Ashrafi, Channeling Radiation of Electrons in Crystal Lattices, Essays on Classical and Quantum Dynamics, Gordon and Breach Science Publishers, 1991.
(Continued)

*Primary Examiner* — Michael P Stafira

(57) ABSTRACT

An apparatus for measuring a concentration of amyloid-beta within a chiral solution includes signal generation circuitry for generating a first signal having an applied first orbital angular momentum signature and applying the first signal to the chiral solution. A detector for receiving the first signal after the first signal passes through the chiral solution and determining the concentration of amyloid-beta within the chiral solution based on a detected second orbital angular momentum signature received from the chiral solution that comprises an amplitude measurement and a phase measurement.

20 Claims, 30 Drawing Sheets

Related U.S. Application Data continuation-in-part of application No. 14/339,836, filed on Jul. 24, 2014, now Pat. No. 9,267,877.

(60) Provisional application No. 62/060,360, filed on Oct. 6, 2014, provisional application No. 61/951,834, filed on Mar. 12, 2014.

(58) Field of Classification Search
CPC ........... G01N 21/59; G01N 2333/4709; G01N 24/00; G01N 2500/00; G01N 33/4833; G01N 33/487; G01N 33/574; G01N 33/5743

See application file for complete search history.

(56) References Cited

U.S. PATENT DOCUMENTS

| | | |
|---|---|---|
| 4,379,409 A | 8/1983 | Primbsch et al. |
| 4,503,336 A | 3/1985 | Hutchin et al. |
| 4,736,463 A | 4/1988 | Chavez |
| 4,862,115 A | 8/1989 | Lee et al. |
| 5,051,754 A | 9/1991 | Newberg |
| 5,220,163 A | 6/1993 | Toughlian et al. |
| 5,222,071 A | 6/1993 | Pezeshki et al. |
| 5,272,484 A | 12/1993 | Labaar |
| 5,543,805 A | 8/1996 | Thaniyavarn |
| 5,555,530 A | 9/1996 | Meehan |
| 6,337,659 B1 | 1/2002 | Kim |
| 6,992,829 B1 | 1/2006 | Jennings et al. |
| 7,577,165 B1 | 8/2009 | Barrett |
| 7,729,572 B1 | 6/2010 | Pepper et al. |
| 7,792,431 B2 | 9/2010 | Jennings et al. |
| 8,432,884 B1 | 4/2013 | Ashrafi |
| 8,503,546 B1 | 8/2013 | Ashrafi |
| 8,559,823 B2 | 10/2013 | Izadpanah et al. |
| 8,811,366 B2 | 8/2014 | Ashrafi |
| 9,077,577 B1 | 7/2015 | Ashrafi |
| 2005/0254826 A1 | 11/2005 | Jennings et al. |
| 2005/0259914 A1 | 11/2005 | Padgett et al. |
| 2007/0038127 A1 | 2/2007 | Goldstein et al. |
| 2010/0013696 A1 | 1/2010 | Schmitt et al. |
| 2010/0327866 A1 | 12/2010 | Albu et al. |
| 2012/0207470 A1 | 8/2012 | Djordevic et al. |
| 2013/0027774 A1 | 1/2013 | Bovino et al. |
| 2013/0235744 A1 | 9/2013 | Chen et al. |
| 2014/0295481 A1 | 10/2014 | Danias et al. |
| 2014/0355624 A1 | 12/2014 | Li et al. |
| 2015/0098697 A1 | 4/2015 | Marom et al. |

OTHER PUBLICATIONS

Solyman Ashrafi, Solar Flux Forecasting Using Mutual Information with an Optimal Delay, Advances in the Astronautical Sciences, American Astronautical Society, vol. 84 Part II, 1993.

Solyman Ashrafi, PCS system design issues in the presence of microwave OFS, Electromagnetic Wave Interactions, Series on Stability, Vibration and Control of Systems, World Scientific, Jan. 1996.

Solyman Ashrafi, Performance Metrics and Design Parameters for an FSO Communications Link Based on Multiplexing of Multiple Orbital-Angular-Momentum Beams, Globecom2014 OWC Workshop, 2014.

Solyman Ashrafi, Optical Communications Using Orbital Angular Momentum Beams, Adv. Opt. Photon. 7, 66-106, Advances in Optics and Photonic, 2015.

Solyman Ashrafi, Performance Enhancement of an Orbital-Angular-Momentum-Based Free-Space Optical Communication Link through Beam Divergence Controlling, OSA Technical Digest (online), paper M2F.6. The Optical Society, 2015.

Solyman Ashrafi, Experimental demonstration of enhanced spectral efficiency of 1.18 symbols/s/Hz using multiple-layer-overlay modulation for QPSK over a 14-km fiber link. OSA Technical Digest (online), paper JTh2A.63. The Optical Society, 2014.

Solyman Ashrafi, Link Analysis of Using Hermite-Gaussian Modes for Transmitting Multiple Channels in a Free-Space Optical Communication System, The Optical Society, vol. 2, No. 4, Apr. 2015.

Solyman Ashrafi, Performance Metrics and Design Considerations for a Free-Space Optical Orbital-Angular-Momentum-Multiplexed Communication Link, The Optical Society, vol. 2, No. 4, Apr. 2015.

Solyman Ashrafi, Demonstration of Distance Emulation for an Orbital-Angular-Momentum Beam. OSA Technical Digest (online), paper STh1F.6. The Optical Society, 2015.

Solyman Ashrafi, Free-Space Optical Communications Using Orbital-Angular-Momentum Multiplexing Combined with MIMO-Based Spatial Multiplexing. Optics Letters, vol. 40, No. 18, Sep. 4, 2015.

Solyman Ashrafi, Enhanced Spectral Efficiency of 2.36 bits/s/Hz Using Multiple Layer Overlay Modulation for QPSK over a 14-km Single Mode Fiber Link. OSA Technical Digest (online), paper SW1M.6. The Optical Society, 2015.

Solyman Ashrafi, Experimental Demonstration of a 400-Gbit/s Free Space Optical Link Using Multiple Orbital-Angular-Momentum Beams with Higher Order Radial Indices. OSA Technical Digest (online), paper SW4M.5. The Optical Society, 2015.

Solyman Ashrafi, Experimental Demonstration of 16-Gbit/s Millimeter-Wave Communications Link using Thin Metamaterial Plates to Generate Data-Carrying Orbital-Angular-Momentum Beams, ICC 2015, London, UK, 2014.

Solyman Ashrafi, Experimental Demonstration of Using Multi-Layer-Overlay Technique for Increasing Spectral Efficiency to 1.18 bits/s/Hz in a 3 Gbit/s Signal over 4-km Multimode Fiber. OSA Technical Digest (online), paper JTh2A.63. The Optical Society, 2015.

Solyman Ashrafi, Experimental Measurements of Multipath-Induced Intra- and Inter-Channel Crosstalk Effects in a Millimeter-Wave Communications Link using Orbital-Angular-Momentum Multiplexing, ICC 2015, London, UK, 2014.

Solyman Ashrafi, Performance Metrics for a Free-Space Communication Link Based on Multiplexing of Multiple Orbital Angular Momentum Beams with Higher Order Radial Indice. OSA Technical Digest (online), paper JTh2A.62. The Optical Society, 2015.

Solyman Ashrafi, 400-Gbit/s Free-Space Optical Communications Link Over 120-meter Using Multiplexing of 4 Collocated Orbital-Angular-Momentum Beams. OSA Technical Digest (online), paper M2F.1. The Optical Society, 2015.

Solyman Ashrafi, Experimental Demonstration of Two-Mode 16-Gbit/s Free-Space mm-Wave Communications Link Using Thin Metamaterial Plates to Generate Orbital Angular Momentum Beams, Optica, vol. 1, No. 6, Dec. 2014.

Solyman Ashrafi, Demonstration of an Obstruction-Tolerant Millimeter-Wave Free-Space Communications Link of Two 1-Gbaud 16-QAM Channels using Bessel Beams Containing Orbital Angular Momentum, Third International Conference on Optical Angular Momentum (ICOAM), Aug. 4-7, 2015, New York USA.

Wang et al: "Terabit free-space data transmission employing orbital angular momentum multiplexing", Nature Photonics, vol. 6, Jul. 2012, pp. 488-496.

Solyman Ashrafi, An Information Theoretic Framework to Increase Spectral Efficiency, IEEE Transactions on Information Theory, vol. XX, No. Y, Oct. 2014, Dallas, Texas.

H. Yao et al, Patch Antenna Array for the Generation of Millimeter-wave Hermite-Gaussian Beams, IEEE Antennas and Wireless Propagation Letters, (pending publication).

Yongxiong Ren et al, Experimental Investigation of Data Transmission Over a Graded-index Multimode Fiber Using the Basis of Orbital Angular Momentum Modes (pending publication).

M. Nouri et al., Perturbations of Laguerre-Gaussian Beams by Chiral Molecules (pending publication).

Solyman Ashrafi, Acoustically induced stresses in elastic cylinders and their visualization, The Journal of the Acoustical Society of America 82(4):1378-1385, Sep. 1987.

Solyman Ashrafi, Splitting of channeling-radiation peaks in strained-layer superlattices, Journal of the Optical Society of America B 8(12), Nov. 1991.

(56) References Cited

OTHER PUBLICATIONS

Solyman Ashrafi, Spurious Resonances and Modelling of Composite Resonators, 37th Annual Symposium on Frequency Control, 1983.

Solyman Ashrafi, Splitting and contrary motion of coherent bremsstrahlung peaks in strained-layer superlattices, Journal of Applied Physics 70:4190-4193, Dec. 1990.

Solyman Ashrafi, Evidence of Chaotic Pattern in Solar Flux Through a Reproducible Sequence of Period-Doubling-Type Bifurcations, Proceedings of Flight Mechanics/Estimation Theory Symposium, National Aeronautics and Space Administration, May 1991.

Solyman Ashrafi, Combining Schatten's Solar Activity Prediction Model with a Chaotic Prediction Model, National Aeronautics and Space Administration, Nov. 1991.

Solyman Ashrafi, Nonlinear Techniques for Forecasting Solar Activity Directly From its Time Series, Proceedings of Flight Mechanics/Estimation Theory Symposium, National Aeronautics and Space Administration, May 1992.

Solyman Ashrafi, Detecting and Disentangling Nonlinear Structure from Solar Flux Time Series, 43rd Congress of the International Astronautical Federation, Aug. 1992.

Solyman Ashrafi, Physical Phaseplate for the Generation of a Millimeter-Wave Hermite-Gaussian Beam, IEEE Antennas and Wireless Propagation Letters, RWS 2016; pp. 234-237.

Solyman Ashrafi; Future Mission Studies: Preliminary Comparisons of Solar Flux Models; NASA Goddard Space Flight Center Flight Dynamics Division; Flight Dynamics Division Code 550; Greenbelt, Maryland; Dec. 1991.

Ren, Y. et al.; Experimental Demonstration of 16 Gbit/s millimeter-wave Communications using MIMO Processing of 2 OAM Modes on Each of Two Transmitter/Receiver Antenna Apertures. In Proc. IEEE GLobal TElecom. Conf. 3821-3826 (2014).

Li, X. et al.; Investigation of interference in multiple-input multiple-output wireless transmission at W band for an optical wireless integration system. Optics Letters 38, 742-744 (2013).

Padgett, Miles J. et al., Divergence of an orbital-angular-momentum-carrying beam upon propagation. New Journal of Physics 17, 023011 (2015).

Mahmouli, F.E. & Walker, D. 4-Gbps Uncompressed Video Transmission over a 60-GHz Orbital Angular Momentum Wireless Channel. IEEE Wireless Communications Letters, vol. 2, No. 2, 223-226 (Apr. 2013).

Vasnetsov, M. V., Pasko, V.A. & Soskin, M.S.; Analysis of orbital angular momentum of a misaligned optical beam; New Journal of Physics 7, 46 (2005).

Byun, S.H., Haji, G.A. & Young, L.E.; Development and application of GPS signal multipath simulator; Radio Science, vol. 37, No. 6, 1098 (2002).

Tamburini, Fabrizio; Encoding many channels on the same frequency through radio vorticity: first experimental test; New Journal of Physics 14, 033001 (2012).

Gibson, G. et al., Free-space information transfer using light beans carrying orbital angular momentum; Optical Express 12, 5448-5456 (2004).

Yan, Y. et al.; High-capacity millimetre-wave communications with orbital angular momentum multiplexing; Nature Communications; 5, 4876 (2014).

Hur, Sooyoung et at.; Millimeter Wave Beamforming for Wireless Backhaul and Access in Small Cell Networks. IEEE Transactions on Communications, vol. 61, 4391-4402 (2013).

Allen, L., Beijersbergen, M., Spreeuw, R.J.C., and Woerdman, J.P.; Orbital Angular Momentum of Light and the Transformation of Laguerre-Gaussian Laser Modes; Physical Review A, vol. 45, No. 11; 8185-8189 (1992).

Anderson, Jorgen Bach; Rappaport, Theodore S.; Yoshida, Susumu; Propagation Measurements and Models for Wireless Communications Channels; 33 42-49 (1995).

Iskander, Magdy F.; Propagation Prediction Models for Wireless Communication Systems; IEEE Transactions on Microwave Theory and Techniques, vol. 50., No. 3, 662-673 (2002).

Wang, Jian, et al.; Terabit free-space data transmission employing orbital angular momentum multiplexing. Nature Photonics; 6, 488-496 (2012).

Katayama, Y., et al.; Wireless Data Center Networking with Steered-Beam mmWave Links; IEEE Wireless Communication Network Conference; 2011, 2179-2184 (2011).

Molina-Terriza, G., et al.; Management of the Angular Momentum of Light: Preparation of Photons in Multidimensional Vector States of Angular Momentum; Physical Review Letters; vol. 88, No. 1; 77, 013601/1-4 (2002).

Rapport, T.S.; Millimeter Wave Mobile Communications for 5G Cellular: It Will Work!; IEEE Access, 1, 335-349 (2013).

PCT: International Preliminary Report on Patentability of PCT/US2015/54281 (related application), Athina Nickitas-Etienne; dated Apr. 11, 2017; 9 pages.

Huang et al., "Phase-shift interference-based wavefront characterization for orbital angular momentum modes." Optics Letters, vol. 38, No. 13, Jul. 1, 2013 (Jul. 1, 2013), pp. 2348, col. 1-2349, col. 2 [online], [retrieved on Nov. 17, 2015] <URL: http://132.66.49.20/~tur/pdfs/176.pdf>.

Karimi et al., "Generating optical orbital angular momentum at visible wavelengths using a plasmonic metasurface." Light: Science & Applications. May 9, 2014 (May 9, 2014) pp. 1-2 [online], [retrieved on Nov. 30, 2015] <URL: http://www.nature.com/lsa/journal/v3/n5/pdf/lsa201448a.pdf>.

Vazin et al., "Efficient derivation of cortical glutamatergic neurons from human pluripotent stem cells: A model system to study neurotoxicity in Alzheimer's disease." Neurobiology of Disease 62, Sep. 18, 2013 (Sep. 18, 2013), pp. 64, col. 2-65, col. 1 [online], [retrieved on Nov. 17, 2015]. <URL: http://www.cchem.berkeley.edu/schaffer/2013%20Publication/Vazin CorticalDiff NBD 13.pdf>.

PCT: International Search Report and Written Opinion of PCT/US2015/54281 (related application), dated Dec. 30, 2015, 37 pgs.

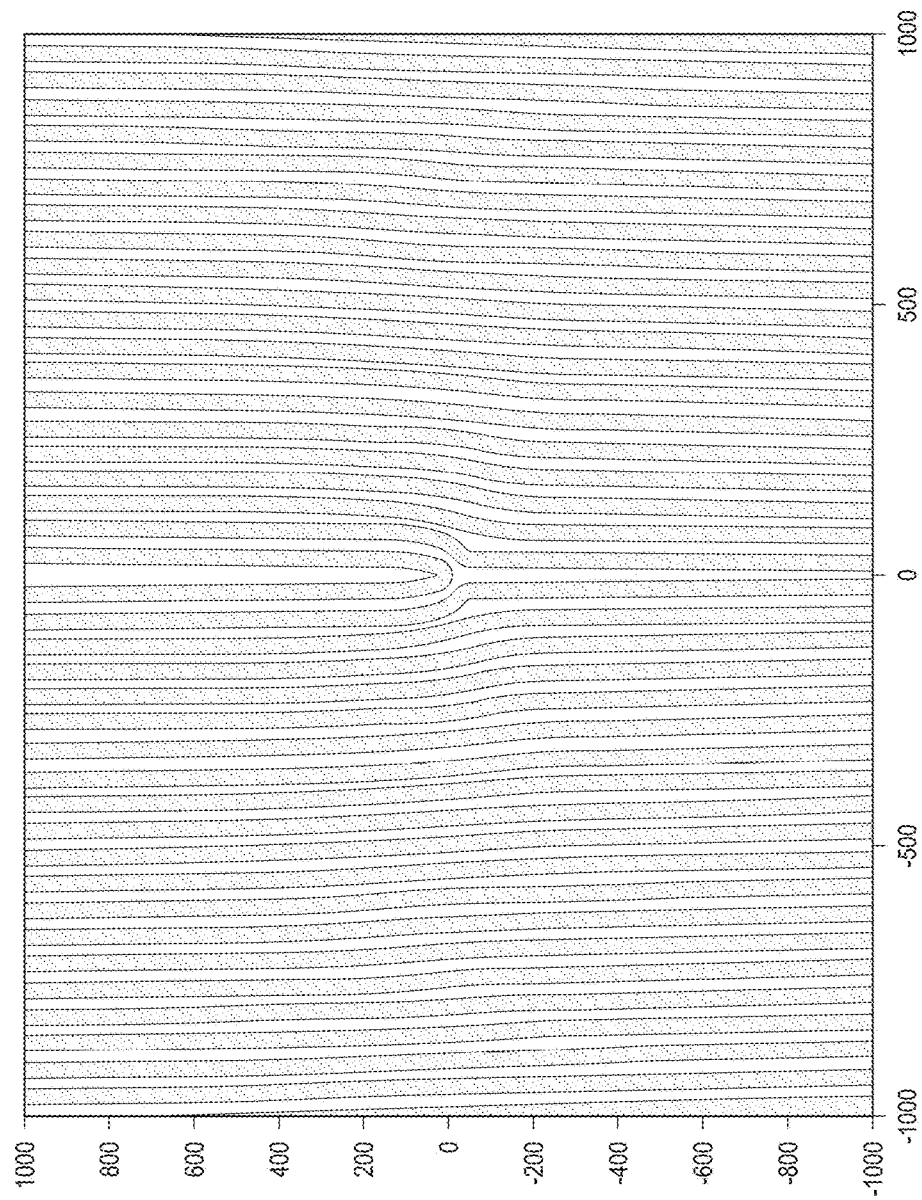

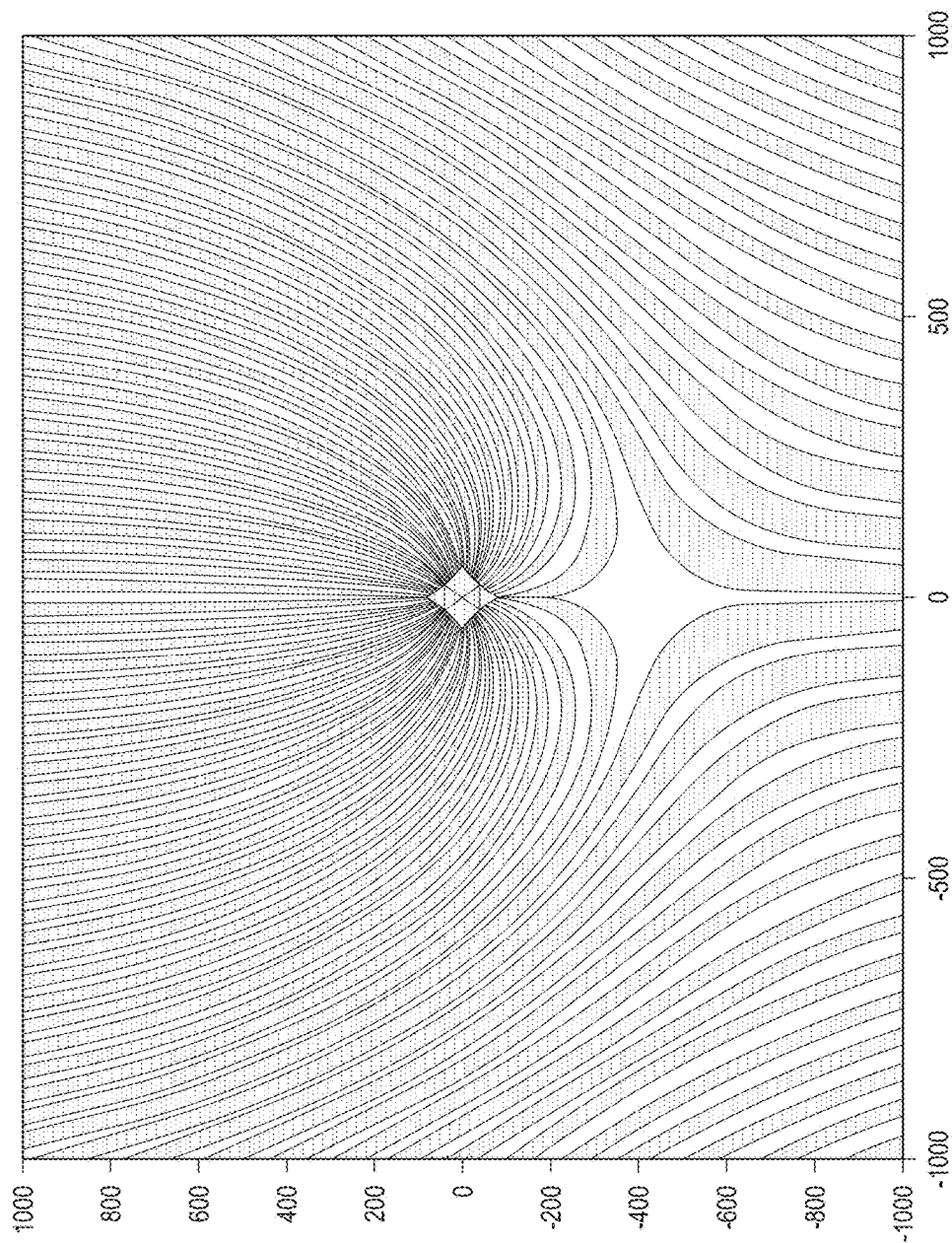

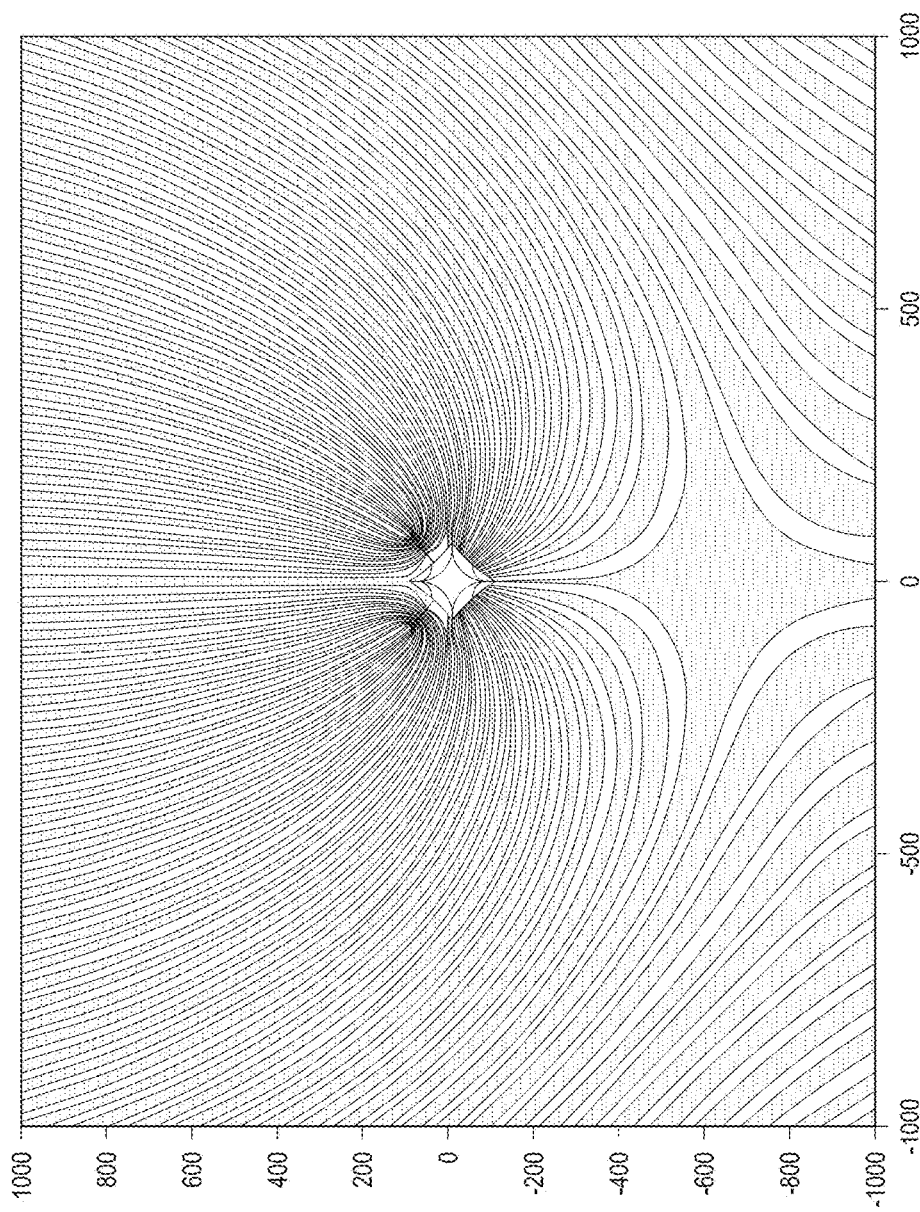

SYSTEM AND METHOD FOR EARLY DETECTION OF ALZHEIMERS BY DETECTING AMYLOID-BETA USING ORBITAL ANGULAR MOMENTUM

CROSS-REFERENCE TO RELATED APPLICATIONS

This application is a Continuation of U.S. application Ser. No. 14/875,507, filed on Oct. 5, 2015, and entitled SYSTEM AND METHOD FOR EARLY DETECTION OF ALZHEIMERS BY DETECTING AMYLOID-BETA USING ORBITAL ANGULAR MOMENTUM, now U.S. Pat. No. 9,784,724 issuing Oct. 10, 2017. U.S. application Ser. No. 14/875,507 claims benefit of U.S. Provisional Application No. 62/060,360, filed on Oct. 6, 2014, and entitled EARLY DETECTION OF ALZHEIMER VIA A NON-INVASIVE EYE SCAN TO DETECT BETA-AMYLOID USING LASER BEAMS WITH ORBITAL ANGULAR MOMENTUM. U.S. application Ser. Nos. 14/875,507 and 62/060,360 and U.S. Pat. No. 9,784,724 are incorporated by reference herein in their entirety.

U.S. application Ser. No. 14/875,507 is also a Continuation-in-Part of U.S. application Ser. No. 14/339,836, filed on Jul. 24, 2014, and entitled SYSTEM AND METHOD FOR MAKING CONCENTRATION MEASUREMENTS WITHIN A SAMPLE MATERIAL USING ORBITAL ANGULAR MOMENTUM, now U.S. Pat. No. 9,267,877 issued on Feb. 23, 2016. U.S. application Ser. No. 14/339,836 claims priority of U.S. Provisional Application No. 61/951,834, filed on Mar. 12, 2014, and entitled CONCENTRATION MEASUREMENTS USING PHOTON ORBITAL ANGULAR MOMENTUM. U.S. application Ser. Nos. 14/875,507; 14/339,836; 61/951,834 and U.S. Pat. No. 9,267,877 are incorporated by reference herein in their entirety.

TECHNICAL FIELD

The present invention relates to the early detection of Alzheimer, and more particularly, to the early detection of Alzheimer by detecting amyloid-beta concentrations using orbital angular momentum.

BACKGROUND

Alzheimer's disease is a serious affliction arising most often in individuals as they reach old age. Symptoms of Alzheimer's include serious memory loss, confusion and behavioral changes. The visible symptoms of Alzheimer's often only began arising in the later stages of the affliction. Changes within an individual's brain having Alzheimer's begin long before the appearance of memory loss and other visible symptoms. Existing treatments and medications have been shown to be more effective when begun upon the early stages of Alzheimer's. Thus, there is a need for providing for the early detection of Alzheimer's.

There are several current methods used in diagnosing Alzheimer's. These include the use of positron emission tomography (PET) imaging that employs ligands which selectively bind to amyloid-beta plaques that are one indication of Alzheimer's. In another technique magnetic resonance imaging (MRI) biomarkers may be detected as an indication of Alzheimer's. These include the reduction of brain volume, specifically hippocampal volume which controls the memory part of the brain. Another indication may be decreased concentrations of amyloid-beta in the cerebral spinal fluid of an individual. Each of these methods have various drawbacks such as being expensive in the case of PET imaging and MRI or invasive and painful in the case of a lumbar puncture required to obtain cerebral spinal fluid.

Concentration measurement of organic and non-organic materials within human tissue is an increasingly important aspect of healthcare for individuals. The development of non-invasive measurement techniques for monitoring biological and metabolic agents within human tissue is an important aspect of diagnosis therapy of various human diseases and may play a key role in the proper management of diseases. One such material relevant to Alzheimer's is amyloid-beta. Thus, there is a need for an improved manner of amyloid-beta detection to better improve detection of early stages of Alzheimer's.

SUMMARY

The present invention, as disclosed and described herein, comprises in one aspect thereof an apparatus for measuring a concentration of amyloid-beta within a chiral solution includes signal generation circuitry for generating a first signal having an applied first orbital angular momentum signature and applying the first signal to the chiral solution. A detector for receiving the first signal after the first signal passes through the chiral solution and determining the concentration of amyloid-beta within the chiral solution based on a detected second orbital angular momentum signature received from the chiral solution that comprises an amplitude measurement and a phase measurement.

BRIEF DESCRIPTION OF THE DRAWINGS

For a more complete understanding, reference is now made to the following description taken in conjunction with the accompanying Drawings in which:

FIGS. 18A-18D illustrate various holograms for use in applying an orbital angular momentum to a plane wave signal;

DETAILED DESCRIPTION

Figure 1:
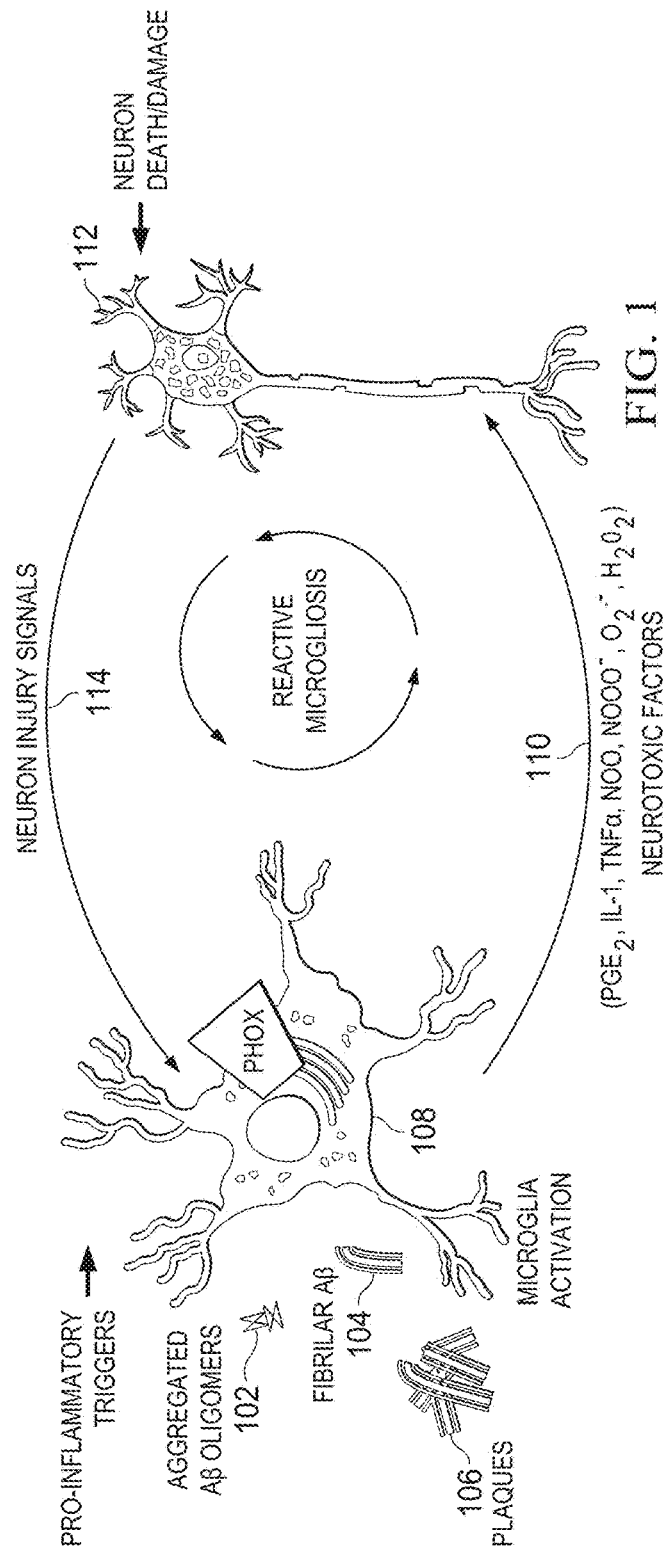
FIG. 1 illustrates the manner in which amyloid-beta deposits affect the brain of an individual.

Referring now to the drawings, wherein like reference numbers are used herein to designate like elements throughout, the various views and embodiments of system and method for making concentration measurements within a sample material using orbital angular momentum are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Alzheimer's is a type of dementia that causes problems with memory, thinking and behavior. Symptoms usually develop slowly and get worse over time, becoming severe enough to interfere with daily tasks. Alzheimer's is the most common form of dementia, a general term for memory loss and other intellectual abilities serious enough to interfere with daily life. Alzheimer's disease accounts for 60 to 80 percent of dementia cases.

Alzheimer's is not a normal part of aging, although the greatest known risk factor is increase aging and the majority of people with Alzheimer's are 65 and older. However, Alzheimer's is not just a disease of old age. Up to 5 percent of people with the disease have early onset Alzheimer's (also known as younger-onset) which often appears when a person is in their 40s or 50s.

Alzheimer's worsens over time. Alzheimer's is a progressive disease, where dementia symptoms gradually worsen over a number of years. In its early stages, memory loss is mild but with late stage Alzheimer's, individuals lose the ability to carry on a conversation and respond to their environment. Alzheimer's is the sixth leading cause of death in the United States. Those with Alzheimer's live an average of 8 years after their symptoms become noticeable to others, but survival can range from 4 to 20 years, depending on age and other health conditions.

Alzheimer's has no current cure, but treatments for symptoms are available and research continues. Although current Alzheimer's treatments cannot stop Alzheimer's from progressing, they can temporarily slow the worsening of dementia symptoms and improve the quality of life for those with Alzheimer's and their caregivers. Today, there is a worldwide effort underway to find better ways to treat the disease, delay its onset and prevent it from developing.

Many people with early onset Alzheimer's are in their 40s and 50s. They have families, careers or are even caregivers themselves when Alzheimer's disease strikes. In the United States, it is estimated that approximately 200,000 people have early onset Alzheimer's.

Since healthcare providers generally don't look for Alzheimer's disease in younger people, getting an accurate diagnosis of early onset Alzheimer's can be a long and frustrating process. Symptoms may be incorrectly attributed to stress or there may be conflicting diagnoses from different healthcare professionals. People who have early onset Alzheimer's may be in any stage of dementia.

Not everyone will experience the same symptoms or progress at the same rate. The following are the seven stages that patients go through when suffering from Alzheimer's. Stage 1 involves no impairment and normal functions. The person does not experience any memory problems in an interview with a medical professional does not show any evidence or symptoms of dementia. Stage 2 only shows very mild cognitive decline and may be a normal age-related change or the earliest signs of Alzheimer's disease. The person may feel as if he or she is having memory lapses experiencing symptoms such as forgetting familiar words or the location of everyday objects. However, no symptoms of the dementia can be detected during a medical examination or by friends, family or coworkers. Stage 3 patients illustrate a mild cognitive decline and this early stage of Alzheimer's can be diagnosed in some, but not all individuals. Friends, families or coworkers begin to notice difficulties. During a detailed medical interview, doctors may be able to detect problems in memory or concentration. Common Stage 3 difficulties include the noticeable problems coming up with the right word or name, trouble remembering names when introduced to new people, having noticeably greater difficulty performing task in social or work settings, forgetting material that one has just read, losing her misplacing a valuable object and increasing trouble with planning or organizing.

A Stage 4 sufferer will exhibit moderate cognitive decline and may be classified as mild or early stage Alzheimer's disease. At this point, a careful medical interview should be able to detect clear-cut symptoms in several areas such as forgetfulness of recent events; impaired ability to perform challenging mental arithmetic, for example, counting backward from 100 by sevens; greater difficulty in forming complex tasks such as planning dinner for guests, paying bills or managing finances, forgetfulness about one's own personal history; and becoming moody or withdrawn, especially in socially or mentally challenging situations. Stage 5 patients illustrate moderately severe cognitive decline and may be classified as moderate or mid-stage Alzheimer's disease. Sufferers exhibit gaps in memory and thinking that are noticeable, and individuals begin to need help with day-to-day activities. At this stage, those with Alzheimer's may be unable to recall their own address or telephone number or the high school or college from which they graduated. They may become confused about where they are or what day it is. They have trouble with less challenging mental arithmetic, such as counting backwards from 40 by subtracting fours or from 20 by 2. They need help choosing proper clothing for the season or the occasion. They still remember significant details about themselves and their family and require no assistance with eating or using the toilet.

Stage 6 sufferers exhibit severe cognitive decline. They are classified as moderately severe or mid-stage Alzheimer's disease. Their memory continues to worsen and personality changes may take place. They need extensive help with daily activities. At this stage, the individuals may lose awareness of recent events as well as their surroundings. They may remember their own name but have difficulty with their personal history. Finally, Stage 7 patients demonstrate very severe cognitive decline and are classified as severe or late stage Alzheimer's disease. In the final stages of Alzheimer's, individuals lose the ability to respond to their environment, to carry on a conversation and eventually to control movement. They may still say words or phrases. The individual needs help with much of their daily personal care including eating or using the toilet. I may also lose the ability to smile, to sit without support and to hold their heads up. Reflexes become abnormal and muscles grow rigid which may impair swallowing.

Alzheimer's disease may be identified by plaques forming on the brain of the patient formed by deposits of amyloid-beta that can result in neuronal death. Amyloid-beta is a peptide that contains between 36-43 amino acids which are found in plaques in Alzheimer's. The most common peptide found in brain plaques in the eye are amyloid beta-42 and amyloid beta-40.

Amyloid-beta is a chiral solution that has been observed to cause orbital angular momentum (OAM) beams to exhibit unique topological evolution when interacting therewith. Given these unique topological features one can detect the amyloid-beta concentration of a given sample based upon a specific signature in both amplitude and phase measurements. Molecular chirality signifies a structural handedness associated with variance under spatial inversion or a combination of inversion and rotation, equivalent to the usual criteria of a lack of any proper axes of rotation. Something is chiral when something cannot be made identical to its reflection. Chiral molecules that are not superimposable on their mirror image are known as Enantiomers. Traditionally, chiral optics engages circularly polarized light, even in the case of optical rotation, interpretation of the phenomenon commonly requires the plane polarized state to be understood as a superposition of circular polarizations with opposite handedness. For circularly polarized light, the left and right forms designate the sign of intrinsic spin angular momentum, ±h and also the helicity of the locus described by the associated electromagnetic field vectors. For this reason its interactions with matter are enantiomerically specific.

The continuous symmetry measure (CSM) is used to evaluate the degree of symmetry of a molecule, or the chirality. This value ranges from 0 to 100. The higher the symmetry value of a molecule the more symmetry distorted the molecule and the more chiral the molecule. The measurement is based on the minimal distance between the chiral molecule and the nearest achiral molecule.

The continuous symmetry measure may be achieved according to the equation:

$$S(G) = 100 \times \min \frac{1}{Nd^2} \sum_{k=1}^{N} |Q_k - \hat{Q}_k|^2$$

$Q_k$: The original structure
$\hat{Q}_k$: The symmetry-operated structure
N: Number of vertices
d: Size normalization factor
*The scale is 0-1 (0-100):
The larger S(G) is, the higher is the deviation from G-symmetry
SG as a continuous chirality measure may be determined according to:

$$S(G) = 100 \times \min \frac{1}{Nd^2} \sum_{k=1}^{N} |Q_k - \hat{Q}_k|^2$$

G: The achiral symmetry point group which minimizes S(G)
Achiral molecule: S(G)=0
An achiral molecule has a value of S(G)=0. The more chiral a molecule is the higher the value of S(G).

The considerable interest in orbital angular momentum has been enhanced through realization of the possibility to engineer optical vortices. Here, helicity is present in the wave-front surface of the electromagnetic fields and the associated angular momentum is termed "orbital". The radiation itself is commonly referred to as a 'twisted' or 'helical' beam. Mostly, optical vortices have been studied only in their interactions with achiral matter—the only apparent exception is some recent work on liquid crystals. It is timely and of interest to assess what new features, if any, can be expected if such beams are used to interrogate any system whose optical response is associated with enantiomerically specific molecules.

We first have to construct in generalized form the criteria for manifestations of chirality in optical interactions. For simplicity, materials with a unique enantiomeric specificity are assumed—signifying a chirality that is intrinsic and common to all molecular components (or chromophores) involved in the optical response. Results for systems of this kind will also apply to single molecule studies. Longer range translation/rotation order can also produce chirality, as for example in twisted nematic crystals, but such mesoscopic chirality cannot directly engender enantiomerically specific interactions. The only exception is where optical waves probe two or more electronically distinct, dissymmetrically oriented but intrinsically achiral molecules or chromophores.

Chiroptical interactions can be distinguished by their electromagnetic origins: for molecular systems in their usual singlet electronic ground state, they involve the spatial variation of the electric and magnetic fields associated with the input of optical radiation. This variation over space can be understood to engage chirality either through its coupling with di-symmetrically placed, neighboring chromophore groups (Kirkwood's two-group model, of limited application) or more generally through the coupling of its associated electric and magnetic fields with individual groups. As chirality signifies a local breaking of parity it permits an interference of electric and magnetic interactions. Even in the two group case, the paired electric interactions of the system correspond to electric and magnetic interactions of the single entity which the two groups comprise. Thus, for convenience, the term 'chiral center' is used in the following to denote either chromophore or molecule.

Referring now to FIG. 1, there is illustrated the manner in which amyloid-beta deposits affects the brain of an individual. Amyloid-beta deposits such as aggregated amyloid-beta oligomers 102, fibrilar amyloid-beta 104 and plaques 106 act as pro-inflammatory triggers on neurons 108 within the brain. These pro-inflammatory triggers cause microglia activation causing the creation of various neurotoxic factors 110 causing neuron death/damage 112. The neuron death/damage 112 causes the creation of injury signals 114.

Figure 2:
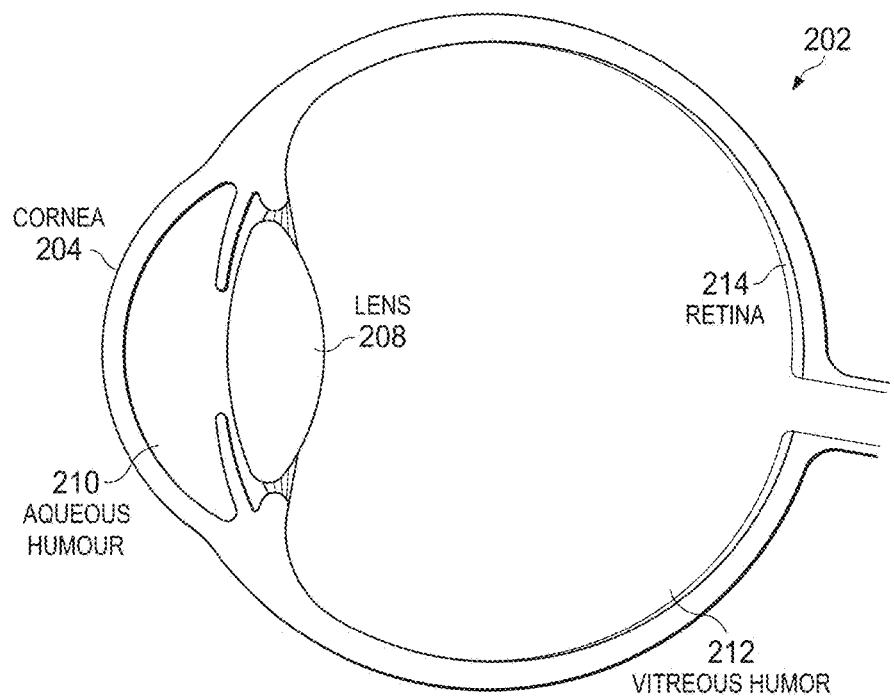
FIG. 2 illustrates a human eye.

One manner for detecting the early onset of Alzheimer's disease has been the detection of amyloid-beta within the eye of a patient. Referring now to FIG. 2, there is illustrated the details of a human eye. The eye 202 is surrounded by a cornea 204. The corneal thickness is approximately 0.449 mm. Behind the cornea 204 is a lens 208. Between the cornea 204 and the lands 208 is the aqueous humor 210. The aqueous humour 210 is a transparent, gelatinous fluid containing low-protein concentrations. The vitreous humour 212 is located behind the lens 208 within the interior portion of the eye. The vitreous humour 212 is a clear gel filling the space between the lens and the retina of the eyeball. When levels of amyloid-beta significantly increase within the body, this has been shown to be an indication of the onset of early stage Alzheimer's. One indication of the increased levels of amyloid-beta is the ability of detecting amyloid-beta within the eye of a patient. When amyloid-beta levels are high within an individual, amyloid-beta may often be detected in the retina 214, the lens 208, the aqueous humor 210 and the vitreous humor 212 of the eye of the patient. This would provide one manner of an early indication of Alzheimer's.

Figure 3:
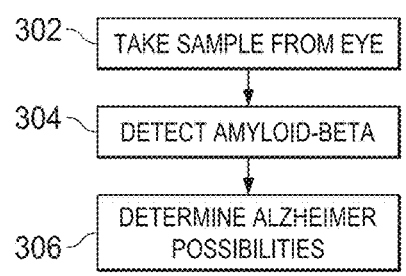
FIG. 3 illustrates a block diagram of a method for detecting Alzheimer's based upon amyloid-beta concentrations within an eye.

Referring now to FIG. 3, there is illustrated a block diagram of a method for detecting Alzheimer's based upon amyloid-beta concentrations within an eye of an individual. Concentration is defined in one example as milligrams of sample (Amyloid-Beta or other material) divided by milliliters of total solution (sample+dilution liquid) for example amyloid-beta plus water. An example would be 0.7 mg amyloid-beta/1.5 total (water+amyloid-beta). Other measures of concentration would also be possible. The process is initiated at step 302 where a sample of material from one of the areas mentioned herein above is obtained. The sample may be physically removed from the eye and place in a container or, alternatively, a detection device may be placed near the eye in order to utilize a sample that is not removed from the eye. Next, the sample is analyzed at step 304 to detect amyloid-beta within the sample. Determinations may then be made at step 306 as to the possibility of the individual having early onset Alzheimer's disease based upon the concentration level of amyloid-beta detected within the sample.

Figure 4A:
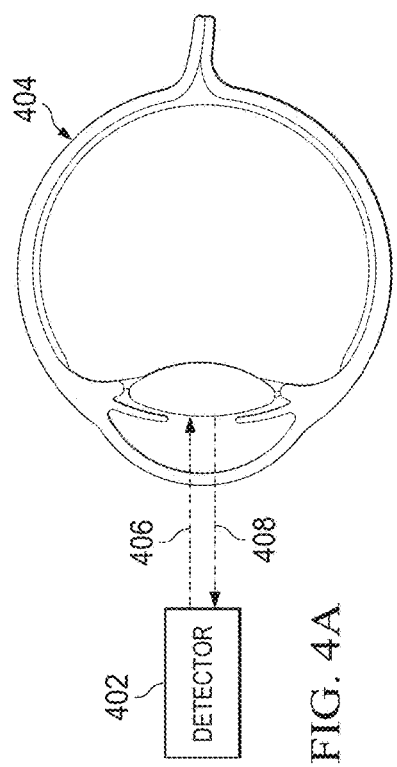
FIG. 4A illustrates an OAM detector detecting amyloid-beta within an eye.

Referring now to FIG. 4A, there is illustrated the use of a detector 402 using an orbital angular momentum (OAM) twisted light beam which is placed in close proximity to an eye 404 in order to detect amyloid-beta therein. OAM is not typically carried by naturally scattered photons which makes the use of OAM twisted beams more accurate when identifying helicity of chiral molecules because the OAM twisted beam does not have ambient light scattered (noise) in detection. The detector 402 would send out a sampling beam 406 into the eye 404 in order to gather information about the concentrations of amyloid-beta therein. The response beam 408 would provide information as will be more fully described herein below about the presence or absence and levels of amyloid-beta within the eye 404.

Figure 4B:
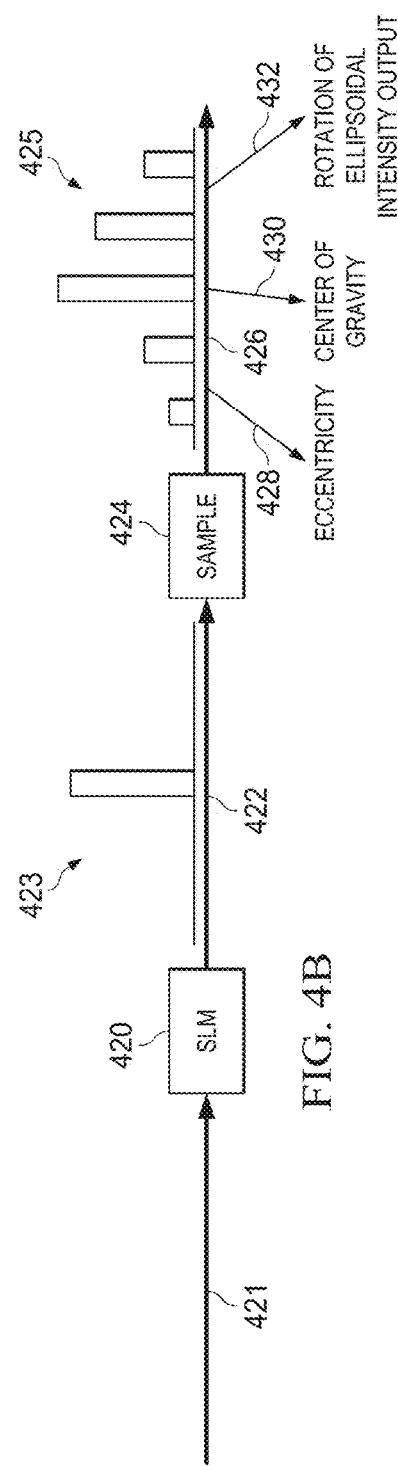
FIG. 4B illustrates the manner in which an OAM generator generates an OAM twisted beam.

Referring now to FIG. 4B illustrates the manner in which an OAM generator 420 may generate an OAM twisted beam 422. The OAM generator 410 may use any number of devices to generate the twisted beam 422 including holograms with an amplitude mask, holograms with a phase mask, Spatial Light Modulators (SLMs) or Digital Light Processors (DLPs). The OAM generator 420 receives a light beam 421 (for example from a laser) that includes a series of plane waves. The OAM generator 420 applies an orbital angular momentum to the beam 422. The beam 422 includes a single OAM mode as illustrated by the intensity diagram 423. The OAM twisted beam 422 is passed through a sample 424 containing an amyloid-beta concentration. The presence of amyloid-beta within the sample 424 will create new OAM mode levels within the intensity diagram 425. Once the beam 422 passes through the sample 424, the output beam 426 will have three distinct signatures associated therewith based on a detection of amyloid-beta concentrations. These signatures include a change in eccentricity 428 of the intensity pattern, a shift or translation 430 in the center of gravity of the intensity pattern and a rotation 432 in three general directions ($\alpha, \beta, \gamma$) of the ellipsoidal intensity pattern output. These three distinct signatures will appear when an amyloid-beta molecule is detected and the manner of changes of these signatures represent concentration levels. The detection of the helicity spectrums from the beam passing through the sample 424 involves detecting the helical wave scatters (forward and backward) from the sample material.

Figure 5:
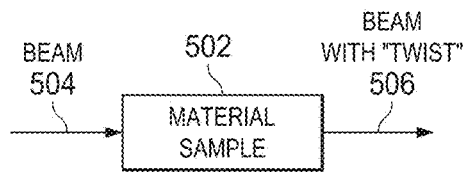
FIG. 5 illustrates a general representation of a manner for determining a concentration of a particular material within a sample using a light beam or other wave.

Referring now to FIG. 5, there is illustrated a general representation of the manner in which the concentration of a particular material sample 502 containing, for example, amyloid beta may be monitored using orbital angular momentum applied to a light beam or other wave transmitted through the material sample 502. The material sample 502 has a beam 504 shined through the length of the material sample 502. As mentioned above, the sample 502 may further be located within an eye or comprise material removed from an eye of a patient. After passing through the material sample 502, the exiting beam 506 leaves the material sample and may be analyzed to determine various concentration characteristics within the material sample 502. The manner in which the different characteristics of the material sample 502 may be determined within the exiting beam 506 is achieved with respect to an analysis of the orbital angular momentum signatures that are imparted to the exiting beam 506 by the concentrations within the material sample 502.

Figure 6:
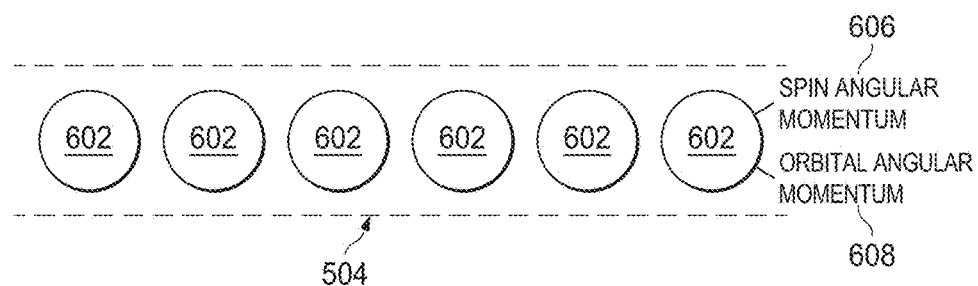
FIG. 6 illustrates a light beam having orbital angular momentum imparted thereto.

Referring now also to FIG. 6, there is illustrated one embodiment of a beam for use with the system. A light beam 504 consists of a stream of photons 602 within the light beam 504. Each photon has an energy $\pm\hbar\omega$ and a linear momentum of $\pm\hbar k$ which is directed along the light beam axis 604 perpendicular to the wavefront. Independent of the frequency, each photon 602 within the light beam has a spin angular momentum 606 of $\pm\hbar$ aligned parallel or antiparallel to the direction of light beam propagation. Alignment of all of the photons 602 spins gives rise to a circularly polarized light beam. In addition to the circular polarization, the light beams also may carry an orbital angular momentum 608 which does not depend on the circular polarization and thus is not related to photon spin.

Figure 7:
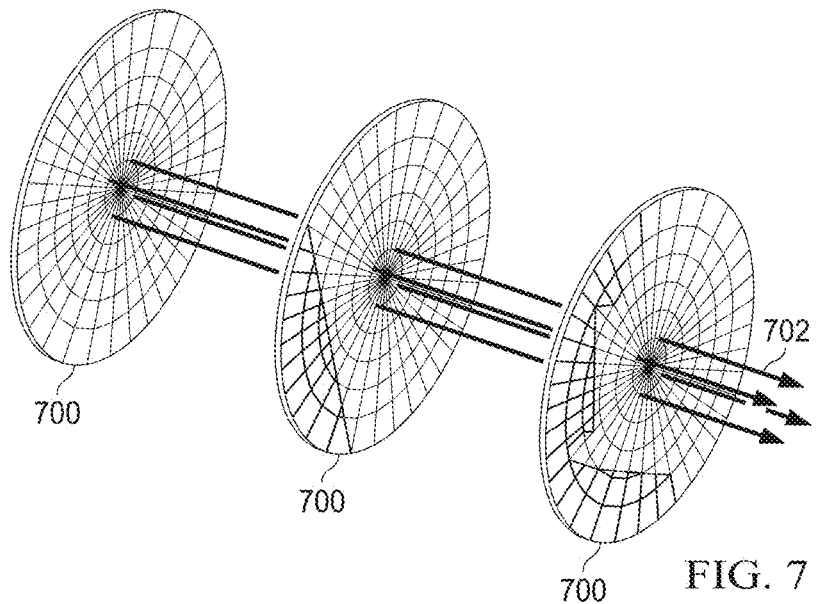
FIG. 7 illustrates a series of parallel wavefronts.

Lasers are widely used in optical experiments as the source of well-behaved light beams of a defined frequency. A laser may be used for providing the light beam 504 as described with respect to FIG. 5. The energy flux in any light beam 504 is given by the Poynting vector which may be calculated from the vector product of the electric and magnetic fields within the light beam. In a vacuum or any isotropic material, the Poynting vector is parallel to the wave vector and perpendicular to the wavefront of the light beam. In a normal laser light, the wavefronts 700 are parallel as illustrated in FIG. 7. The wave vector and linear momentum of the photons are directed along the axis in a z direction 702. The field distributions of such light beams are paraxial solutions to Maxwell's wave equation but although these simple beams are the most common, other possibilities exist.

Figure 8:
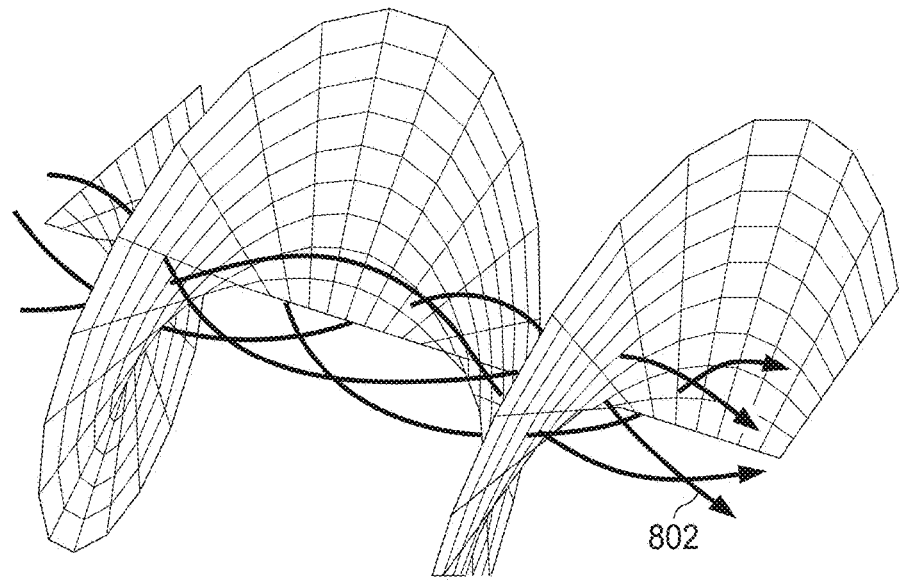
FIG. 8 illustrates a wavefront having a Poynting vector spiraling around a direction of propagation of the wavefront.

For example, beams that have l intertwined helical fronts are also solutions of the wave equation. The structure of these complicated beams is difficult to visualize, but their form is familiar from the l=3 fusilli pasta. Most importantly, the wavefront has a Poynting vector and a wave vector that spirals around the light beam axis direction of propagation as illustrated in FIG. 8 at 802.

A Poynting vector has an azimuthal component on the wave front and a non-zero resultant when integrated over the beam cross-section. The spin angular momentum of circularly polarized light may be interpreted in a similar way. A beam with a circularly polarized planer wave front, even though it has no orbital angular momentum, has an azimuthal component of the Poynting vector proportional to the radial intensity gradient. This integrates over the cross-section of the light beam to a finite value. When the beam is linearly polarized, there is no azimuthal component to the Poynting vector and thus no spin angular momentum.

Thus, the momentum of each photon 602 within the light beam 504 has an azimuthal component. A detailed calculation of the momentum involves all of the electric fields and magnetic fields within the light beam, particularly those electric and magnetic fields in the direction of propagation of the beam. For points within the beam, the ratio between the azimuthal components and the z components of the momentum is found to be l/kr. (where l=the helicity or orbital angular momentum; k=wave number $2\pi/\lambda$; r=the radius vector.) The linear momentum of each photon 602 within the light beam 504 is given by $\hbar k$, so if we take the cross product of the azimuthal component within a radius vector, r, we obtain an orbital momentum for a photon 602 of $l\hbar$. Note also that the azimuthal component of the wave vectors is l/r and independent of the wavelength.

Figure 9:
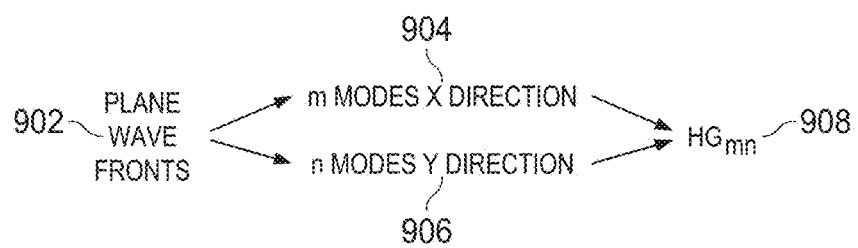
FIG. 9 illustrates a plane wavefront.
Figure 10:
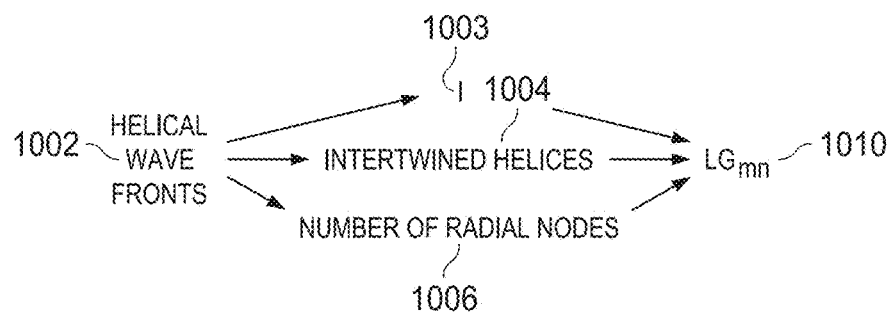
FIG. 10 illustrates a helical wavefront.

Referring now to FIGS. 9 and 10, there are illustrated plane wavefronts and helical wavefronts. Ordinarily, laser beams with plane wavefronts 902 are characterized in terms of Hermite-Gaussian modes. These modes have a rectangular symmetry and are described by two mode indices m 904 and n 906. There are m nodes in the x direction and n nodes in the y direction. Together, the combined modes in the x and y direction are labeled $HG_{mn}$ 908. In contrast, as shown in FIG. 10 beams with helical wavefronts 1002 are best characterized in terms of Laguerre-Gaussian modes which are described by indices I 1003, the number of intertwined helices 1004, and p, the number of radial nodes 1006. The Laguerre-Gaussian modes are labeled $LG_{mn}$ 1010. For l≠0, the phase singularity on a light beam 904 results in 0 on axis intensity. When a light beam 904 with a helical wavefront is also circularly polarized, the angular momentum has orbital and spin components, and the total angular momentum of the light beam is (l±h) per photon.

Using the orbital angular momentum state of the transmitted energy signals, physical information can be embedded within the electromagnetic radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x) \text{the}$$

where $\nabla$ is the del operator, E is the electric field intensity and B is the magnetic flux density. Using these equations, we can derive 23 symmetries/conserve quantities from Maxwell's original equations. However, there are only ten well-known conserve quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3 x (|E|^2 + c^2 |B|^2)$$

$$\frac{dU^{mech}}{dt} + \frac{dU^{em}}{dt} + \oint_{s'} d^2 x' \hat{n}' \cdot S = 0$$

The space symmetry, i.e., the conservation of system linear momentum representing the electromagnetic Doppler shift can be represented by the equations:

$$P = \sum_i m_i \gamma_i v_i + \varepsilon_0 \int d^3x (E \times B)$$

$$\frac{dp^{mech}}{dt} + \frac{dp^{em}}{dt} + \oint_{s'} d^2x' \hat{n}' \cdot T = 0$$

The conservation of system center of energy is represented by the equation:

$$R = \frac{1}{H} \sum_i (x_i - x_0) m_i \gamma_i c^2 + \frac{\varepsilon_0}{2H} \int d^3x (x - x_0)(|E^2| + c^2|B^2|)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{s'} d^2x' \hat{n}' \cdot M = 0$$

For radiation beams in free space, the EM field angular momentum $J^{em}$ can be separated into two parts:

$$J^{em} = \varepsilon_0 \int_{V'} d^3x' (E^* \times A) + \varepsilon_0 \int_{V'} d^3x' E_i [(x'-x_0) \times \nabla] A_i$$

For each singular Fourier mode in real valued representation:

$$J^{em} = -i\frac{\varepsilon_0}{2\omega} \int_{V'} d^3x' (E^* \times E) - i\frac{\varepsilon_0}{2\omega} \int_{V'} d^3x' E_i [(x' - x_0) \times \nabla] E_i$$

The first part is the EM spin angular momentum $S^{em}$, its classical manifestation is wave polarization. And the second part is the EM orbital angular momentum $L^{em}$ its classical manifestation is wave helicity. In general, both EM linear momentum $P^{em}$, and EM angular momentum $J^{em} = L^{em} + S^{em}$ are radiated all the way to the far field.

By using Poynting theorem, the optical vorticity of the signals may be determined according to the optical velocity equation:

$$\frac{\partial U}{\partial t} + \nabla \cdot S = 0,$$

where S is the Poynting vector $$S = 1/4(E \times H^* + E^* \times H),$$

and U is the energy density $$U = 1/4(\varepsilon|E|^2 + \mu_0|H|^2),$$

with E and H comprising the electric field and the magnetic field, respectively, and $\varepsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left( \frac{E \times H^* + E^* \times H}{\varepsilon|E|^2 + \mu_0|H|^2} \right)$$

Figure 11:
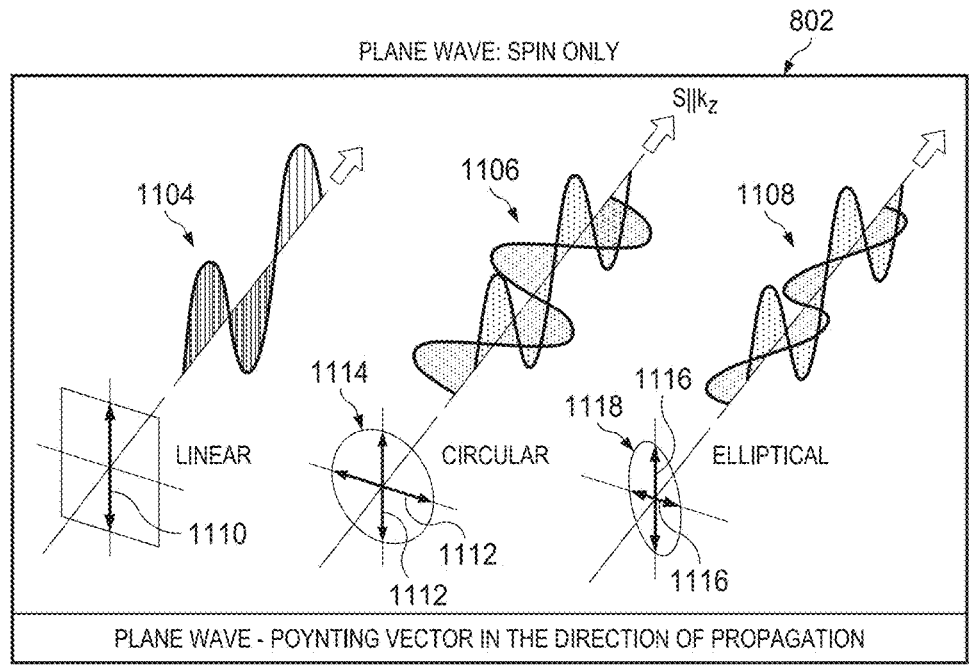
FIG. 11 illustrates a plane wave having only variations in the spin vector.
Figure 12:
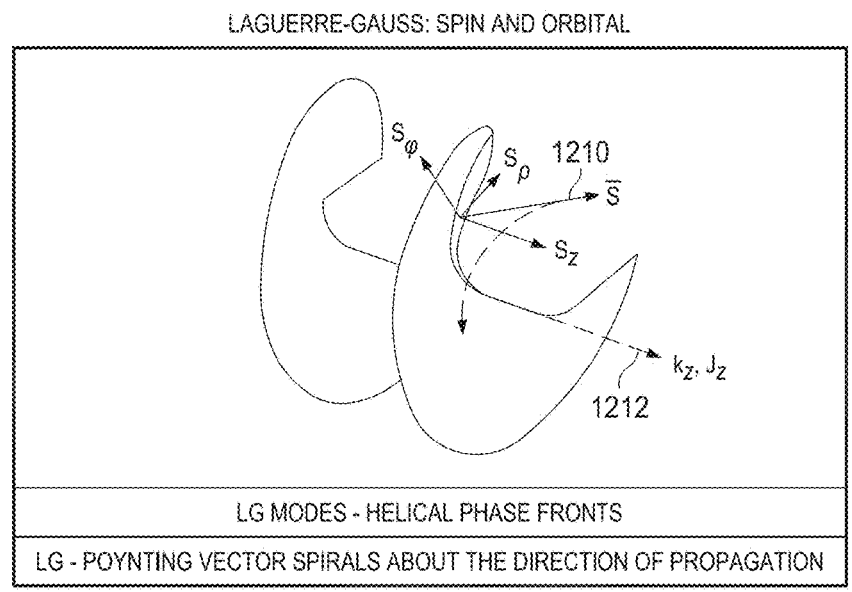
FIG. 12 illustrates the application of a unique orbital angular momentum to a wave.

Referring now to FIGS. 11 and 12, there are illustrated the manner in which a signal and an associated Poynting vector of the signal vary in a plane wave situation (FIG. 11) where only the spin vector is altered, and in a situation wherein the spin and orbital vectors are altered in a manner to cause the Poynting vector to spiral about the direction of propagation (FIG. 12).

In the plane wave situation, illustrated in FIG. 11, when only the spin vector of the plane wave is altered, the transmitted signal may take on one of three configurations. When the spin vectors are in the same direction, a linear signal is provided as illustrated generally at 1104. It should be noted that while 1104 illustrates the spin vectors being altered only in the x direction to provide a linear signal, the spin vectors can also be altered in the y direction to provide a linear signal that appears similar to that illustrated at 1104 but in a perpendicular orientation to the signal illustrated at 1104. In linear polarization such as that illustrated at 1104, the vectors for the signal are in the same direction and have a same magnitude.

Within a circular polarization as illustrated at 1106, the signal vectors 1112 are 90 degrees to each other but have the same magnitude. This causes the signal to propagate as illustrated at 1106 and provide the circular polarization 1114 illustrated in FIG. 11. Within an elliptical polarization 1108, the signal vectors 1116 are also 90 degrees to each other but have differing magnitudes. This provides the elliptical polarizations 1118 illustrated for the signal propagation 408. For the plane waves illustrated in FIG. 11, the Poynting vector is maintained in a constant direction for the various signal configurations illustrated therein.

The situation in FIG. 12 illustrates when a unique orbital angular momentum is applied to a signal. When this occurs, Poynting vector S 1210 will spiral around the general direction of propagation 1212 of the signal. The Poynting vector 1210 has three axial components $S_\varphi$, $S_p$ and $S_z$ which vary causing the vector to spiral about the direction of propagation 612 of the signal. The changing values of the various vectors comprising the Poynting vector 1210 may cause the spiral of the Poynting vector to be varied in order to enable signals to be transmitted on a same wavelength or frequency as will be more fully described herein. Additionally, the values of the orbital angular momentum indicated by the Poynting vector 1210 may be measured to determine concentrations associated with particular materials being processed by a concentration scanning mechanism.

Figure 13A:
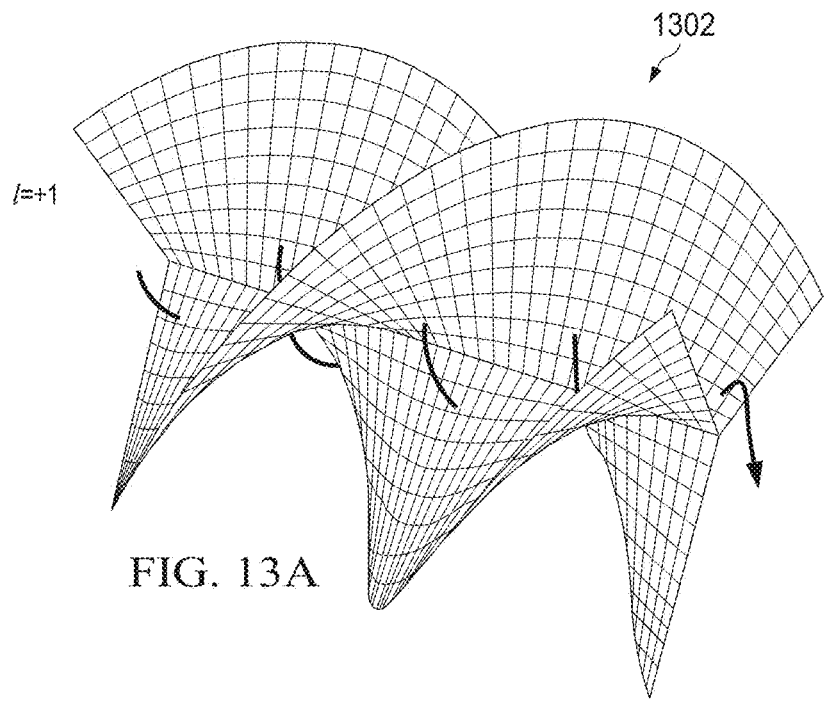
FIGS. 13A-13C illustrate the differences between signals having different orbital angular momentum applied thereto.
Figure 13B:
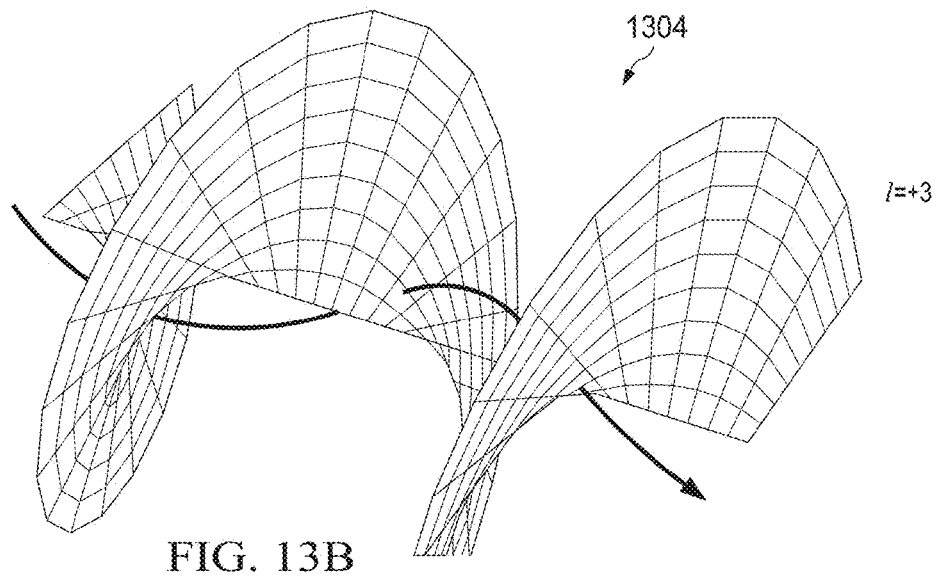
Figure 13C:
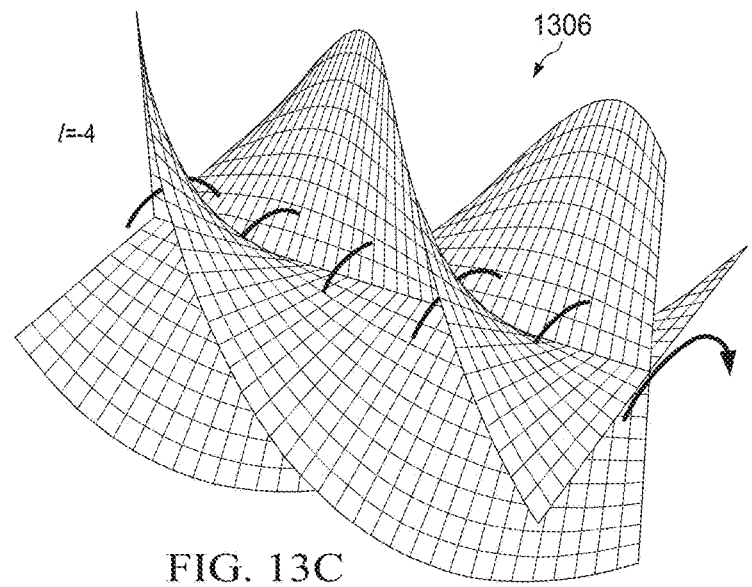

FIGS. 13A-13C illustrate the differences in signals having a different helicity (i.e., orbital angular momentum applied thereto). The differing helicities would be indicative of differing concentration of materials within a sample that a beam was being passed through. By determining the particular orbital angular momentum signature associated with a signal, the concentration amounts of the material could be determined. Each of the spiraling Poynting vectors associated with a signal 1302, 1304 and 1306 provides a different-shaped signal. Signal 1302 has an orbital angular momentum of +1, signal 1304 has an orbital angular momentum of +3 and signal 1306 has an orbital angular momentum of −4. Each signal has a distinct orbital angular momentum and associated Poynting vector enabling the signal to be indicative of a particular concentration of material that is associated with the detected orbital angular momentum. This allows determinations of concentrations of various types of materials to be determined from a signal since the orbital angular momentums are separately detectable and provide a unique indication of the concentration of the particular material that has affected the orbital angular momentum of the signal transmitted through the sample material.

Figure 14:
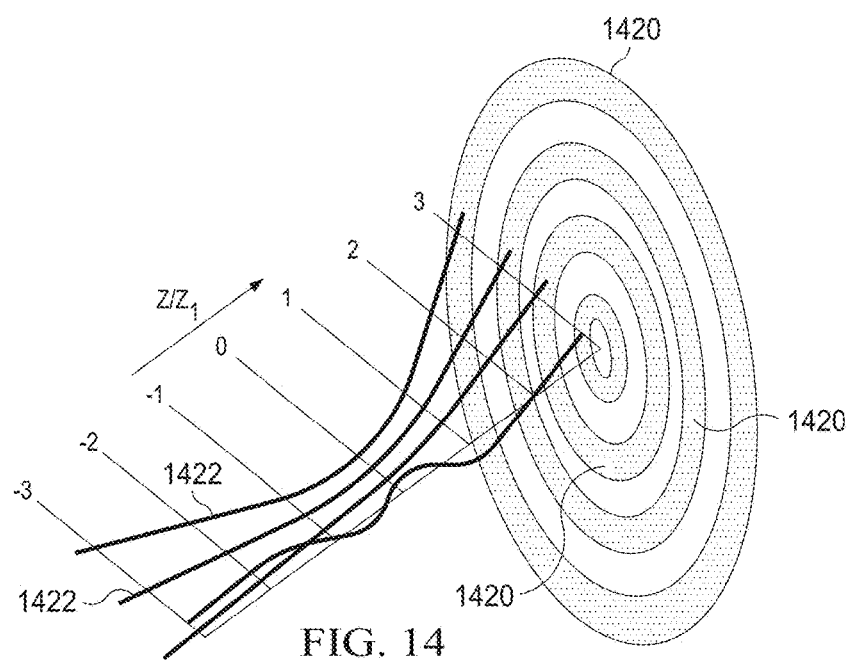
FIG. 14 illustrates the propagation of Poynting vectors for various Eigen modes.

FIG. 14 illustrates the propagation of Poynting vectors for various Eigen modes. Each of the rings 1420 represents a different Eigen mode or twist representing a different orbital angular momentum. Each of the different orbital angular momentums is associated with a particular concentration of a particular material. Detection of orbital angular momentums provide an indication of the associated material concentration that is being monitored by the apparatus. Each of the rings 1420 represents a different concentration of a selected material that is being monitored. Each of the Eigen modes has a Poynting vector 1422 for generating the rings indicating different material concentrations.

Figure 15:
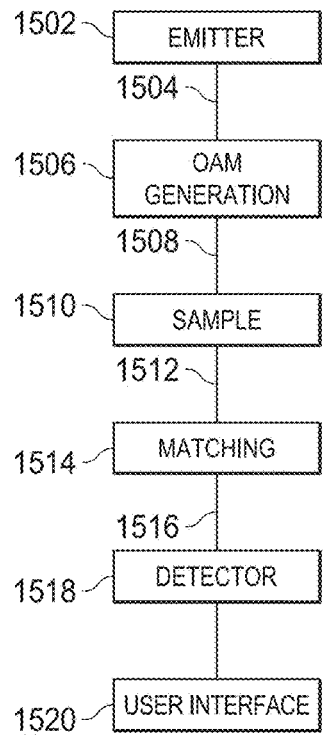
FIG. 15 illustrates a block diagram of an apparatus for providing concentration measurements of various materials using orbital angular momentum.

Referring now to FIG. 15, there is illustrated a block diagram of the apparatus for providing concentration measurements of various materials responsive to the orbital angular momentum detected by the apparatus in accordance with the principles described herein above. An emitter 1502 transmits wave energy 1504 that comprises a series of plane waves. The emitter 1502 may provide a series of plane waves such as those describes previously with respect to FIG. 7. The orbital angular momentum generation circuitry 1506 generates a series of waves having an orbital angular momentum applied to the waves 1508 in a known manner. The orbital angular momentum generation circuitry 1506 may utilize holograms or some other type of orbital angular momentum generation process as will be more fully described herein below. The OAM generation circuitry 1506 may be generated by transmitting plane waves through a spatial light modulator (SLM), an amplitude mask or a phase mask. The orbital angular momentum twisted waves 1508 are applied to a sample material 1510 under test. The sample material 1510 contains a material, and the concentration of the material is determined via a concentration detection apparatus in accordance with the process described herein.

A series of output waves 1512 from the sample material 1510 exit the sample and have a particular orbital angular momentum imparted thereto as a result of the concentration of the particular material under study within the sample material 1510. The output waves 1512 are applied to a matching module 1514 that includes a mapping aperture for amplifying a particular orbital angular momentum generated by the specific material under study. The matching module 1514 will amplify the orbital angular momentums associated with the particular concentration of material that is detected by the apparatus. The amplified OAM waves 1516 are provided to a detector 1518. The detector 1518 detects OAM waves relating to the concentration of a material within the sample and provides this concentration information to a user interface 1520. The detector 1518 may utilize a camera to detect distinct topological features from the beam passing through the amyloid-beta sample. The user interface 1520 interprets the concentration information and provides relevant concentration indication to an individual or a recording device.

Figure 16:
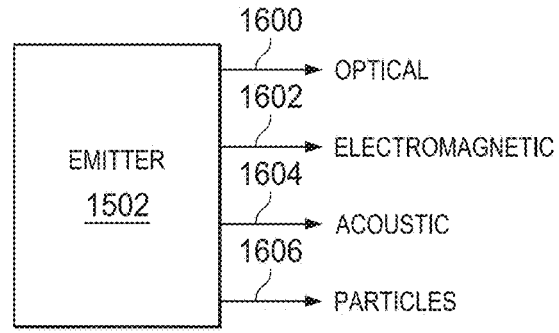
FIG. 16 illustrates an emitter of the system of FIG. 14.

Referring now to FIG. 16, there is more particularly illustrated the emitter 1502. The emitter 1502 may emit a number of types of energy waves 1504 to the OAM generation module 1506. The emitter 1502 may emit optical waves 1600, electromagnetic waves 1602, acoustic waves 1604 or any other type of particle waves 1606. The emitted waves 1504 are plane waves such as those illustrated in FIG. 7 having no orbital angular momentum applied thereto and may come from a variety of types of emission devices and have information included therein. In one embodiment, the emission device may comprise a laser. Plane waves have wavefronts that are parallel to each other having no twist or helicity applied thereto, and the orbital angular momentum of the wave is equal to 0. The Poynting vector within a plane wave is completely in line with the direction of propagation of the wave.

Figure 17:
FIG. 17 illustrates a fixed orbital angular momentum generator of the system of FIG. 14.
Figure 18B:
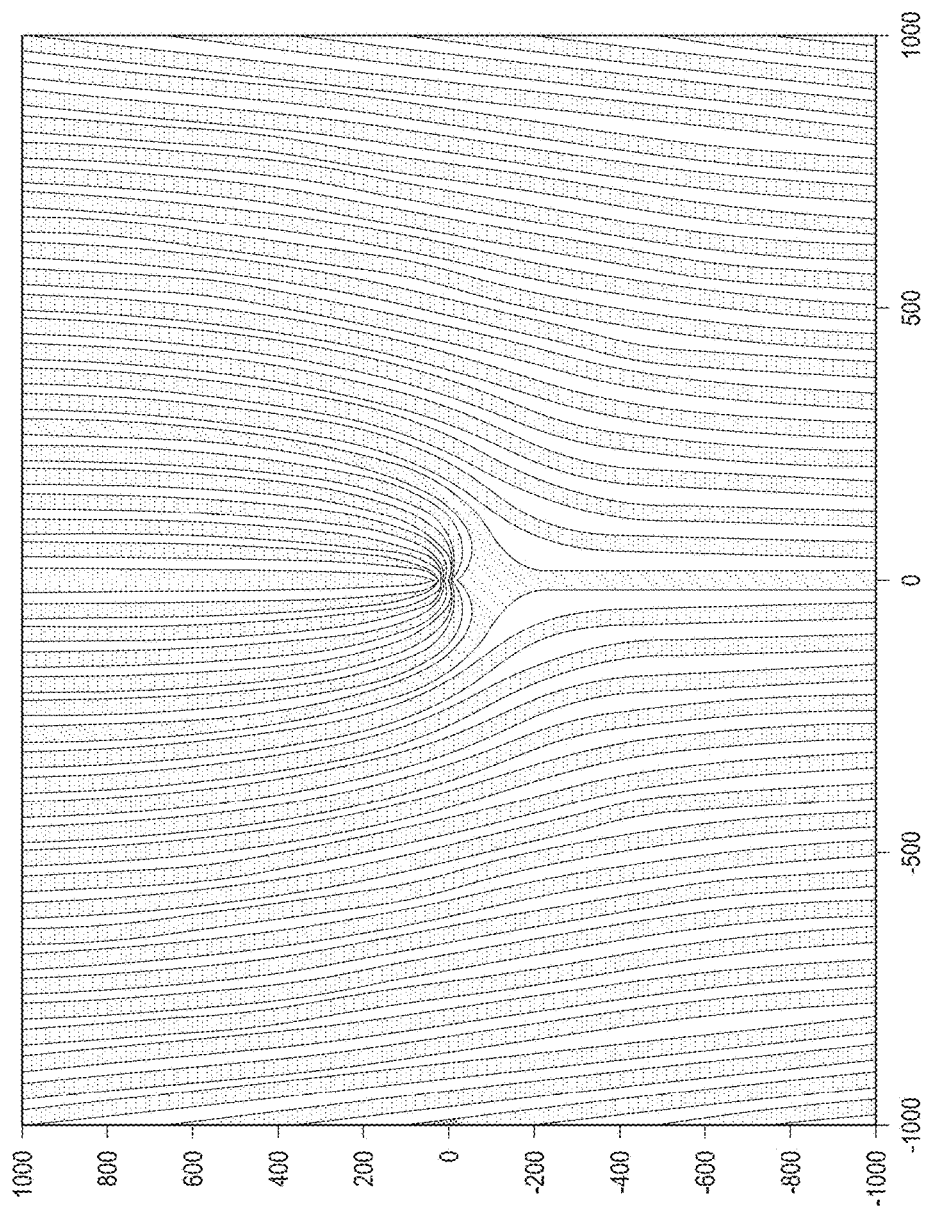

The OAM generation module 1506 processes the incoming plane wave 1504 and imparts a known orbital angular momentum onto the plane waves 1504 provided from the emitter 1502. The OAM generation module 1506 generates twisted or helical electromagnetic, optic, acoustic or other types of particle waves from the plane waves of the emitter 702. A helical wave 1508 is not aligned with the direction of propagation of the wave but has a procession around direction of propagation as shown in FIG. 17. The OAM generation module 1506 may comprise in one embodiment a fixed orbital angular momentum generator 1702 as illustrated in FIG. 17. The fixed orbital angular momentum generator 1702 receives the plane waves 1504 from the emitter 1502 and generates an output wave 1704 having a fixed orbital angular momentum applied thereto.

The fixed orbital angular momentum generator 1702 may in one embodiment comprise a holographic image for applying the fixed orbital angular momentum to the plane wave 1504 in order to generate the OAM twisted wave 904. Various types of holographic images may be generated in order to create the desired orbital angular momentum twist to an optical signal that is being applied to the orbital angular momentum generator 1502. Various examples of these holographic images are illustrated in FIG. 18a-18d. In one embodiment, the conversion of the plane wave signals transmitted from the emitter 1502 by the orbital angular momentum generation circuitry 706 may be achieved using holographic images.

Figure 19:
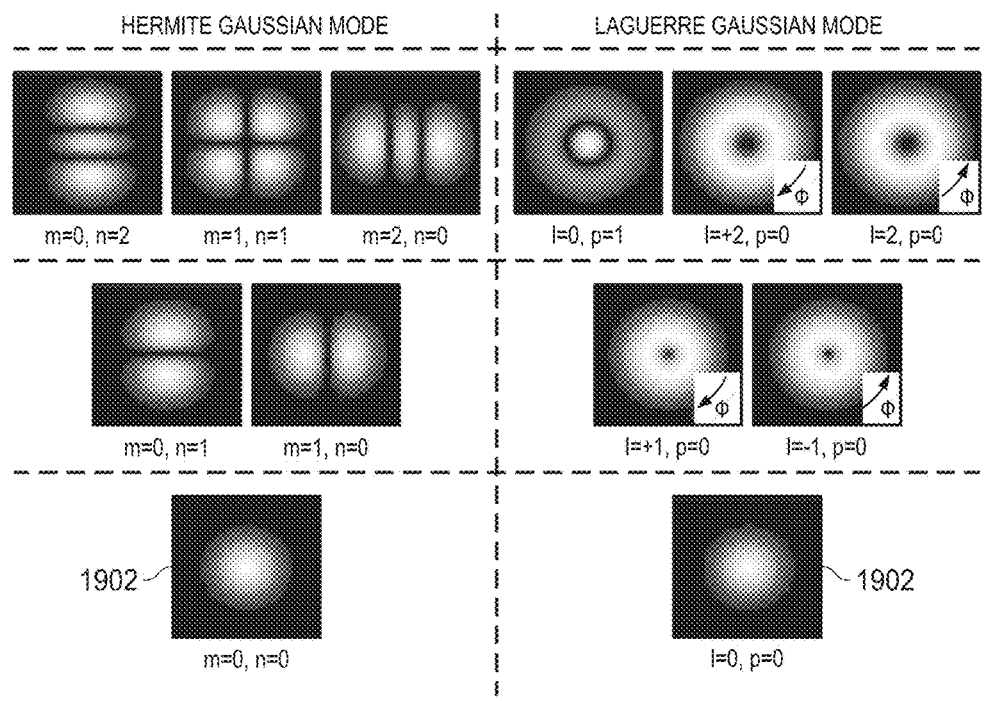
FIG. 19 illustrates the relationship between Hermite-Gaussian modes and Laguerre-Gaussian modes.

Most commercial lasers emit an $HG_{00}$ (Hermite-Gaussian) mode 1902 (FIG. 19) with a planar wave front and a transverse intensity described by a Gaussian function. Although a number of different methods have been used to successfully transform an $HG_{00}$ Hermite-Gaussian mode 1902 into a Laguerre-Gaussian mode 1904, the simplest to understand is the use of a hologram.

The cylindrical symmetric solution $u_{pl}$ $(r,\varphi,z)$ which describes Laguerre-Gaussian beams, is given by the equation:

$$u_{pl}(r, \phi, z) = \frac{C}{(1+z^2/z_R^2)^{1/2}} \left[\frac{r\sqrt{2}}{w(z)}\right]^l L_p^l \left[\frac{2r^2}{w^2(z)}\right] \exp\left[\frac{-r^2}{w^2(z)}\right]$$

$$\exp\left[\frac{-ikr^2 z}{2(z^2+z_R^2)}\right] \exp(-il\phi) \times \exp\left[i(2p+l+1)\tan^{-1}\frac{z}{z_R}\right]$$

Where $z_R$ is the Rayleigh range, w(z) is the radius of the beam, $L_P$ is the Laguerre polynomial, C is a constant, and the beam waist is at z=0.

In its simplest form, a computer generated hologram is produced from the calculated interference pattern that results when the desired beam intersects the beam of a conventional laser at a small angle. The calculated pattern is transferred to a high resolution holographic film. When the developed hologram is placed in the original laser beam, a diffraction pattern results. The first order of which has a desired amplitude and phase distribution. This is one manner for implementing the OAM generation module 1506. A number of examples of holographic images for use within a OAM generation module are illustrated with respect to FIGS. 18a-18d.

There are various levels of sophistication in hologram design. Holograms that comprise only black and white areas with no grayscale are referred to as binary holograms. Within binary holograms, the relative intensities of the two interfering beams play no role and the transmission of the hologram is set to be zero for a calculated phase difference between zero and $\pi$, or unity for a phase difference between $\pi$ and $2\pi$. A limitation of binary holograms is that very little of the incident power ends up in the first order diffracted spot, although this can be partly overcome by blazing the grating. When mode purity is of particular importance, it is also possible to create more sophisticated holograms where the contrast of the pattern is varied as a function of radius such that the diffracted beam has the required radial profile.

A plane wave shining through the holographic images 1802 will have a predetermined orbital angular momentum shift applied thereto after passing through the holographic image 1802. OAM generator 1502 is fixed in the sense that a same image is used and applied to the beam being passed through the holographic image. Since the holographic image 1802 does not change, the same orbital angular momentum is always applied to the beam being passed through the holographic image 1802. While FIG. 18a-18d illustrate a number of embodiments of various holographic images that might be utilized within the orbital angular momentum generator 1502, it will be realized that any type of holographic image 1802 may be utilized in order to achieve the desired orbital angular momentum within an beam being shined through the image 1802.

Figure 20:
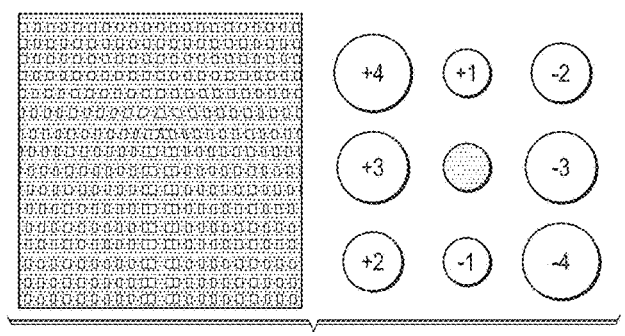
FIG. 20 illustrates super-imposed holograms for applying orbital angular momentum to a signal.

In another example of a holographic image illustrated in FIG. 20, there is illustrated a hologram that utilizes two separate holograms that are gridded together to produce a rich number of orbital angular momentum (l). The superimposed holograms of FIG. 20 have an orbital angular momentum of l=1 and l=3 which are superimposed upon each other to compose the composite vortex grid 1602. The holograms utilized may also be built in a manner that the two holograms are gridded together to produce a varied number of orbital angular momentums (l) not just on a line (l=+1, l=0, l=−1) but on a square which is able to identify the many variables more easily. Thus, in the example in FIG. 16, the orbital angular momentums along the top edge vary from +4 to +1 to −2 and on the bottom edge from +2 to −1 to −4. Similarly, along the left edge the orbital angular momentums vary from +4 to +3 to +2 and on the right edge from −2 to −3 to −4. Across the horizontal center of the hologram the orbital angular momentums provided vary from +3 to 0 to −3 and along the vertical axis vary from +1 to 0 to −1. Thus, depending upon the portion of the grid a beam may pass through, varying orbital angular momentum may be achieved.

Figure 21:
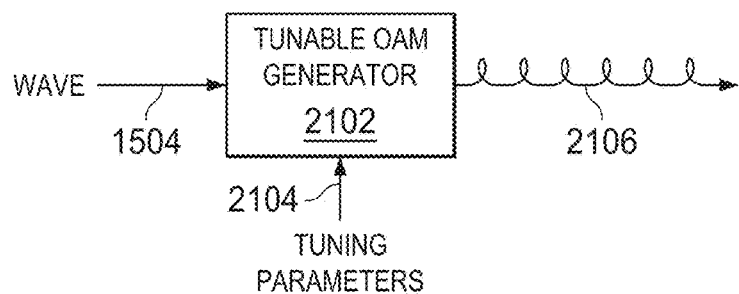
FIG. 21 illustrates a tunable orbital angular momentum generator for use in the system of FIG. 11.

Referring now to FIG. 21, in addition to a fixed orbital angular momentum generator, the orbital angular momentum generation circuitry 1506 may also comprise a tunable orbital angular momentum generator circuitry 2102. The tunable orbital angular momentum generator 2102 receives the input plane wave 1504 but additionally receives one or more tuning parameters 2104. The tuning parameters 2104 tune the tunable OAM generator 2102 to apply a selected orbital angular momentum so that the tuned OAM wave 2106 that is output from the OAM generator 2102 has a selected orbital angular momentum value applied thereto.

This may be achieved in any number of fashions. In one embodiment, illustrated in FIG. 22, the tunable orbital angular momentum generator 2102 may include multiple hologram images 2202 within the tunable OAM generator 2102. The tuning parameters 2104 enable selection of one of the holographic images 2206 in order to provide the desired OAM wave twisted output signal 2106 through a selector circuit 2204. Alternatively, the gridded holographic image such as that described in FIG. 16 may be utilized and the beam shined on a portion of the gridded image to provide the desired OAM output. The tunable OAM generator 2102 has the advantage of being controlled to apply a particular orbital angular momentum to the output orbital angular momentum wave 2106 depending upon the provided input parameter 2104. This enables the concentrations of a variety of different materials to be monitored, or alternatively, for various different concentrations of the same material to be monitored.

Figure 22:
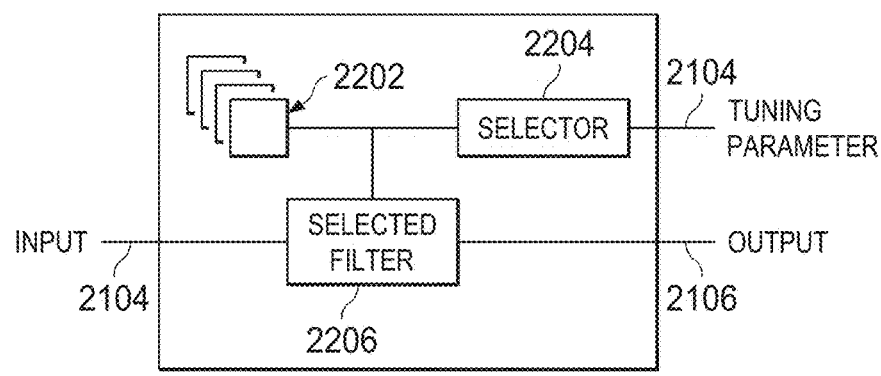
FIG. 22 illustrates a block diagram of a tunable orbital angular momentum generator including multiple hologram images therein.

Referring now to FIG. 22, there is more particularly implemented a block diagram of a tunable orbital angular momentum generator 2102. The generator 2102 includes a plurality of holographic images 2202 for providing orbital angular momentums of various types to a provided light signal. These holographic images 2202 are selected responsive to a selector circuitry 2204 that is responsive to the input tuning parameters 2104. The selected filter 2206 comprises the holographic image that has been selected responsive to the selector controller 2204 and receives the input plane waves 1504 to provide the tuned orbital angular momentum wave output 2106. In this manner, signals having a desired orbital angular momentum may be output from the OAM generation circuitry 1506.

Figure 23:
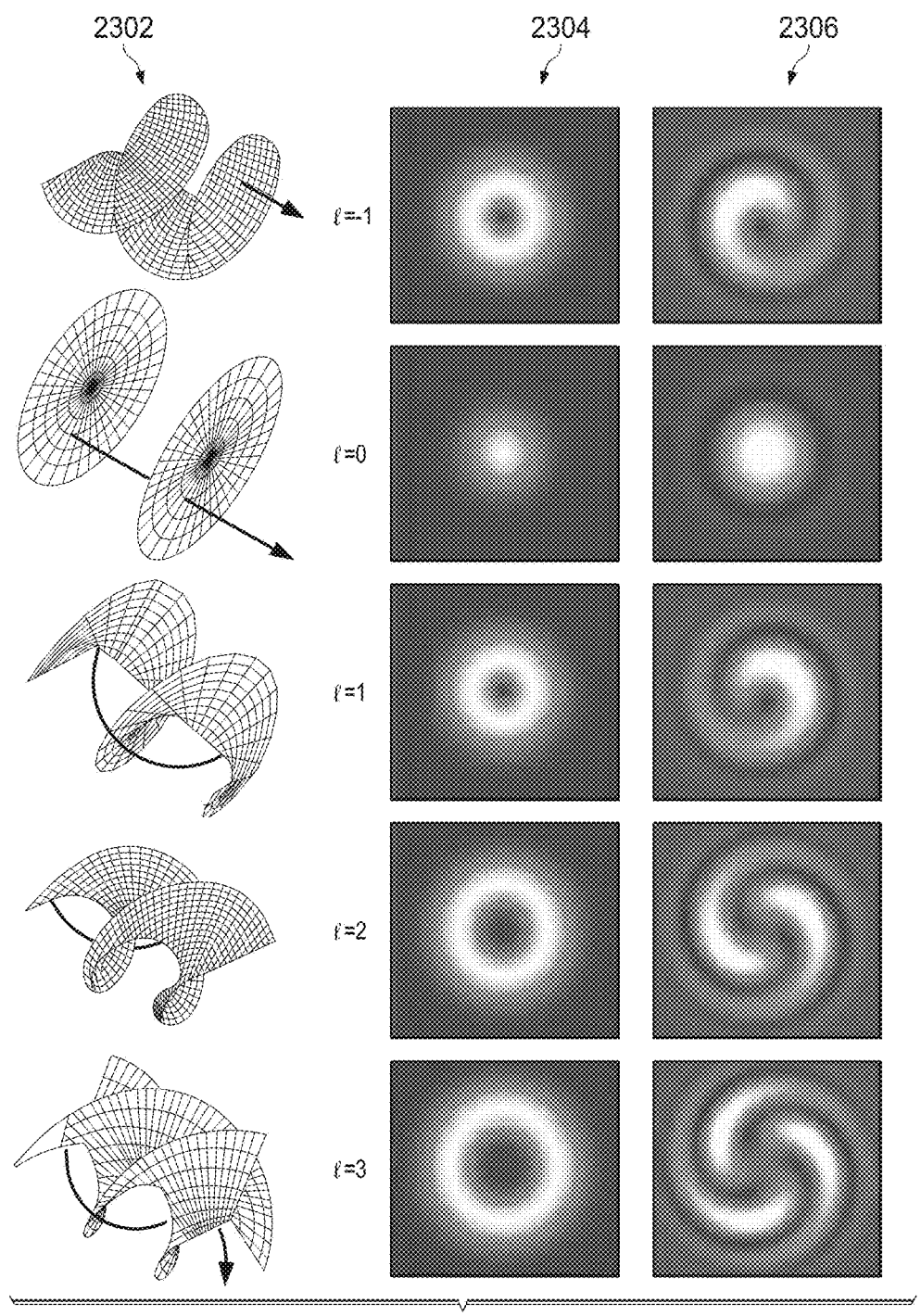
FIG. 23 illustrates the manner in which the output of the OAM generator may be varied by applying different orbital angular momentums thereto.

Referring now to FIG. 23, there is illustrated the manner in which the output of the OAM generator 1506 may vary a signal by applying different orbital angular momentum thereto. FIG. 23 illustrates helical phase fronts in which the Poynting vector is no longer parallel to the beam axis and thus has an orbital angular momentum applied thereto. In any fixed radius within the beam, the Poynting vector follows a spiral trajectory around the axis. Rows are labeled by l, the orbital angular momentum quantum number, L=lh is the beams orbital angular momentum per photon within the output signal. For each l, the left column 2302 is the light beam's instantaneous phase. The center column 2304 comprises the angular intensity profiles and the right column 2306 illustrates what occurs when such a beam interferes with a plane wave and produces a spiral intensity pattern. This is illustrated for orbital angular momentums of −1, 0, 1, 2 and 3 within the various rows of FIG. 23.

Figure 24:
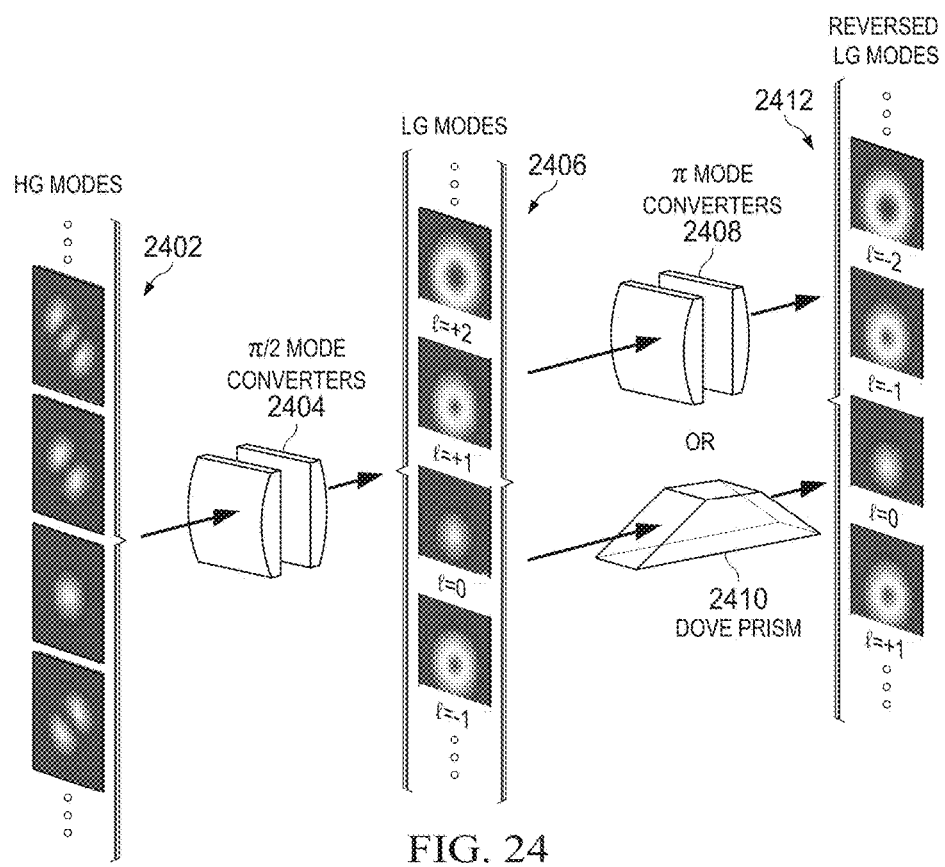
FIG. 24 illustrates an alternative manner in which the OAM generator may convert a Hermite-Gaussian beam to a Laguerre-Gaussian beam.

Referring now to FIG. 24, there is illustrated an alternative manner in which the OAM generator 1506 may convert a Hermite-Gaussian beam output from an emitter 1502 to a Laguerre-Gaussian beams having imparted therein an orbital angular momentum using mode converters 2404 and a Dove prism 2410. The Hermite-Gaussian mode plane waves 2402 are provided to a $\pi/2$ mode convertor 2404. The $\pi/2$ mode convertor 2404 produce beams in the Laguerre-Gaussian modes 2406. The Laguerre-Gaussian modes beams 2406 are applied to either a it mode convertor 2408 or a dove prism 2410 that reverses the mode to create a reverse Laguerre-Gaussian mode signal 2412.

Figure 25:
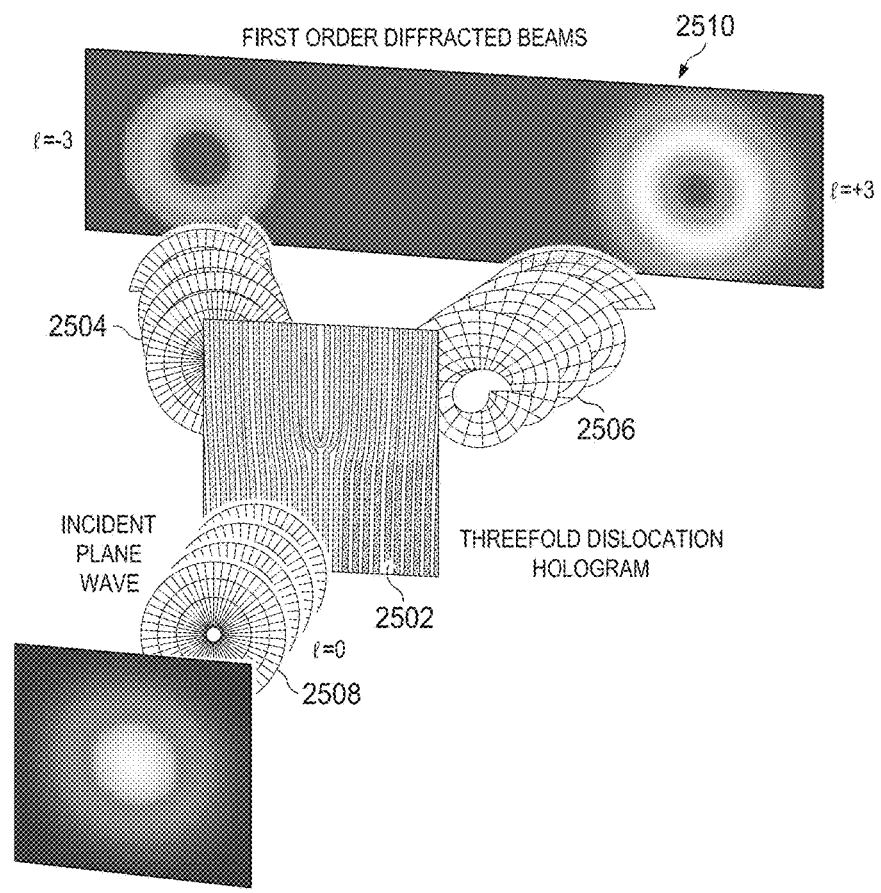
FIG. 25 illustrates the manner in which holograms within an OAM generator may twist a beam of light.

Referring now to FIG. 25, there is illustrated the manner in which holograms within the OAM generator 1506 generate a twisted light beam. A hologram 2502 can produce light beam 2504 and light beam 2506 having helical wave fronts and associated orbital angular momentum lh per photon. The appropriate hologram 2502 can be calculated or generated from the interference pattern between the desired beam form 2504, 2506 and a plane wave 2508. The resulting holographic pattern within the hologram 2502 resembles a diffraction grating, but has a l-pronged dislocation at the beam axis. When the hologram is illuminated with the plane wave 2508, the first-order diffracted beams 2504 and 2506 have the desired helical wave fronts to provide the desired first ordered diffracted beam display 2510.

Figure 26:
FIG. 26 illustrates the manner in which a sample receives an OAM twisted wave and provides an output wave having a particular OAM signature.

Referring now to FIG. 26, there is more particularly illustrated the manner in which the sample 1510 receives the input OAM twisted wave 1508 provided from the OAM generator 1506 and provides an output OAM wave 1512 having a particular OAM signature associated therewith that depends upon the concentration of a particular monitored material within the sample 1510. The sample 1510 may comprise any sample that is under study and may be in a solid form, liquid form or gas form. The sample material 1510 that may be detected using the system described herein may comprise a variety of different materials. As stated previously, the material may comprise liquids such as blood, water, oil or chemicals. The various types of carbon bondings such as C—H, C—O, C—P, C—S or C—N may be provided for detection. The system may also detect various types of bondings between carbon atoms such as a single bond (methane or Isooctane), dual bond items (butadiene and benzene) or triple bond carbon items such as acetylene.

The sample 1510 may include detectable items such as organic compounds including carbohydrates, lipids (cylcerol and fatty acids), nucleic acids (C,H,O,N,P) (RNA and DNA) or various types of proteins such as polyour of amino $NH_2$ and carboxyl COOH or aminos such as tryptophan, tyrosine and phenylalanine. Various chains within the samples 1510 may also be detected such as monomers, isomers and polymers. Enzymes such as ATP and ADP within the samples may be detected. Substances produced or released by glands of the body may be in the sample and detected. These include items released by the exocrine glands via tube/ducts, endocrine glands released directly into blood samples or hormones. Various types of glands that may have their secretions detected within a sample 1510 include the hypothalamus, pineal and pituitary glands, the parathyroid and thyroid and thymus, the adrenal and pancreas glands of the torso and the hormones released by the ovaries or testes of a male or female.

The sample 1510 may also be used for detecting various types of biochemical markers within the blood and urine of an individual such as melanocytes and keratinocytes. The sample 1510 may include various parts of the body to detect defense substances therein. For example, with respect to the skin, the sample 1510 may be used to detect carotenoids, vitamins, enzymes, b-carotene and lycopene. With respect to the eye pigment, the melanin/eumelanin, dihydroxyindole or carboxylic may be detected. The system may also detect various types of materials within the body's biosynthetic pathways within the sample 1510 including hemoglobin, myoglobin, cytochromes, and porphyrin molecules such as protoporphyrin, coporphyrin, uroporphyrin and nematoporphyrin. The sample 1510 may also contain various bacterias to be detected such as propion bacterium, acnes. Also various types of dental plaque bacteria may be detected such as porphyromonos gingivitis, prevotella intremedi and prevotella nigrescens. The sample 1510 may also be used for the detection of glucose in insulin within a blood sample 1510.

The sample 1510 may also include amyloid-beta detection. Detection of amyloid-beta within the sample may then be used for determinations of early onset Alzheimer's. Higher levels of amyloid-beta may provide an indication of the early stages of Alzheimer's.

Figure 27:
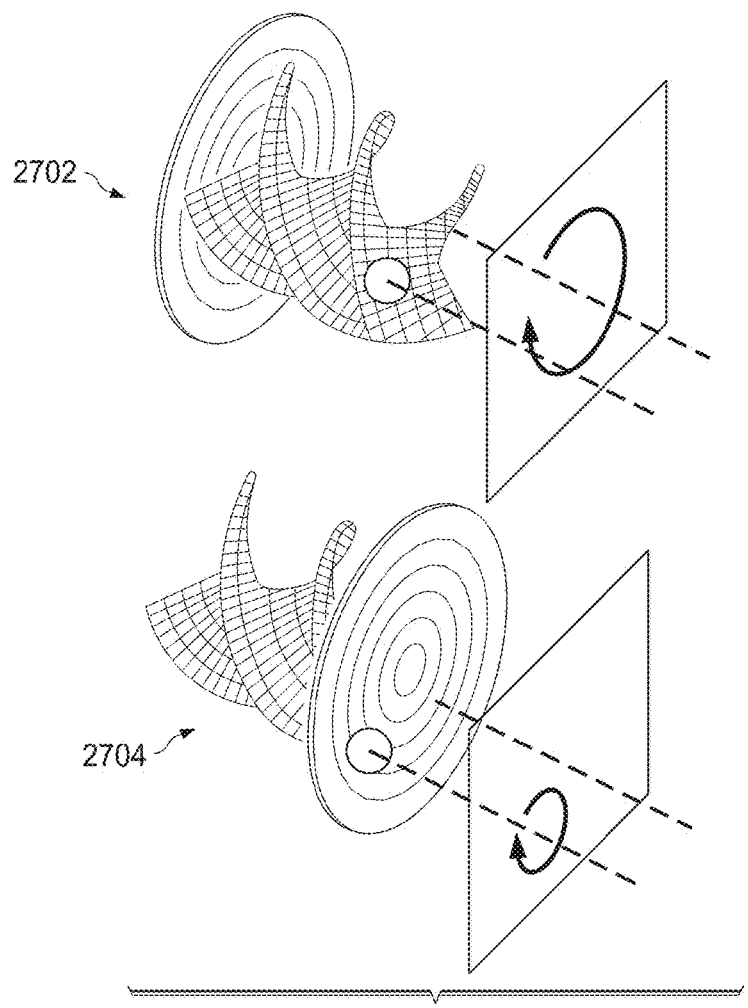
FIG. 27 illustrates the manner in which orbital angular momentum interacts with a molecule around its beam axis.

The orbital angular momentum within the beams provided within the sample 1510 may be transferred from light to matter molecules depending upon the rotation of the matter molecules. When a circularly polarized laser beam with a helical wave front traps a molecule in an angular ring of light around the beam axis, one can observe the transfer of both orbital and spin angular momentum. The trapping is a form of optical tweezing accomplished without mechanical constraints by the ring's intensity gradient. The orbital angular momentum transferred to the molecule makes it orbit around the beam axis as illustrated at 2702 of FIG. 27. The spin angular momentum sets the molecule spinning on its own axis as illustrated at 2704.

The output OAM wave 1512 from the sample 1510 will have an orbital angular momentum associated therewith that is different from the orbital angular momentum provided on the input OAM wave 1508. The difference in the output OAM wave 1512 will depend upon the material contained within the sample 1510 and the concentration of these materials within the sample 1510. Differing materials of differing concentration will have unique orbital angular momentums associated therewith. Thus, by analyzing the particular orbital angular momentum signature associated with the output OAM wave 1512, determinations may be made as to the materials present within the sample 1510 and the concentration of these materials within the sample may also be determined.

Figure 28:
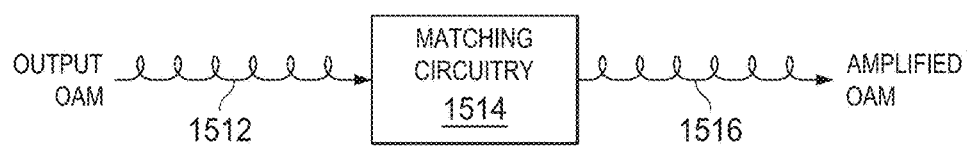
FIG. 28 illustrates a block diagram of the matching circuitry for amplifying a received orbital angular momentum signal.

Referring now to FIG. 28, the matching module 1514 receives the output orbital angular momentum wave 1512 from the sample 1510 that has a particular signature associated therewith based upon the orbital angular momentum imparted to the waves passing through the sample 1510. The matching module 1514 amplifies the particular orbital angular momentum of interest in order to provide an amplified wave having the desired orbital angular momentum of interest 1516 amplified. The matching module 1514 may comprise a matching aperture that amplifies the detection orbital angular momentum associated with a specific material or characteristic that is under study. The matching module 1514 may in one embodiment comprise a holographic filter such as that described with respect to FIGS. 18a-18d in order to amplify the desired orbital angular momentum wave of interest. The matching module 1514 is established based upon a specific material of interest that is trying to be detected by the system. The matching module 1514 may comprise a fixed module using holograms as illustrated in FIGS. 18a-18d or a tunable module in a manner similar to that discussed with respect to the OAM generation module 1506. In this case, a number of different orbital angular momentums could be amplified by the matching module in order to detect differing materials or differing concentration of materials within the sample 1510. Other examples of components for the matching module 1514 include the use of quantum dots, nanomaterials or metamaterials in order to amplify any desired orbital angular momentum values within a received wave form from the sample 1510.

Figure 29:
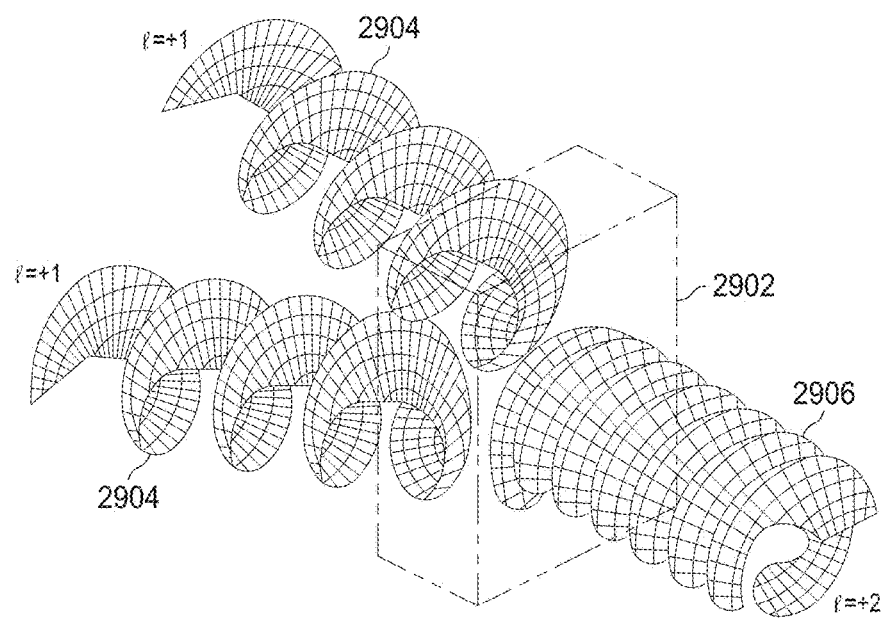
FIG. 29 illustrates the manner in which the matching module may use non-linear crystals in order to generate a higher order orbital angular momentum light beam.

Referring now to FIG. 29, the matching module 1514 rather than using holographic images in order to amplify the desired orbital angular momentum signals may use non-linear crystals in order to generate higher orbital angular momentum light beams. Using a non-linear crystal 2902, a first harmonic orbital angular momentum beam 2904 may be applied to a non-linear crystal 2902. The non-linear crystal 2902 will create a second order harmonic signal 2906.

Figure 30:
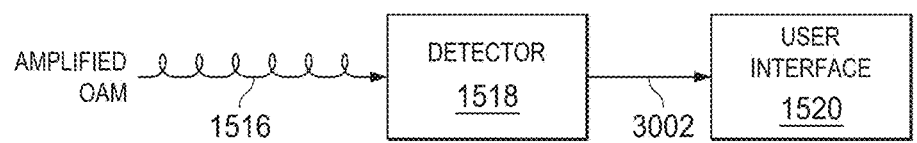
FIG. 30 illustrates a block diagram of an orbital angular momentum detector and user interface.

Referring now to FIG. 30, there is more particularly illustrated the detector 1518 to which the amplified orbital angular momentum wave 1516 from the matching circuit 1514 in order that the detector 1518 may extract desired OAM measurements 2602. The detector 1518 receives the amplified OAM waves 1516 and detects and measures observable changes within the orbital angular momentum of the emitted waves due to the concentration of a particular material under study within the sample 1510. The detector 1518 is able to measure observable changes within the emitted amplified OAM wave 1516 from the state of the input OAM wave 1508 applied to the sample 1510. The extracted OAM measurements 3002 are applied to the user interface 1520. The manner in which the detector 1518 may detect differences within the orbital angular momentum is more particularly illustrates with respect to FIG. 31-33.

Figure 31:
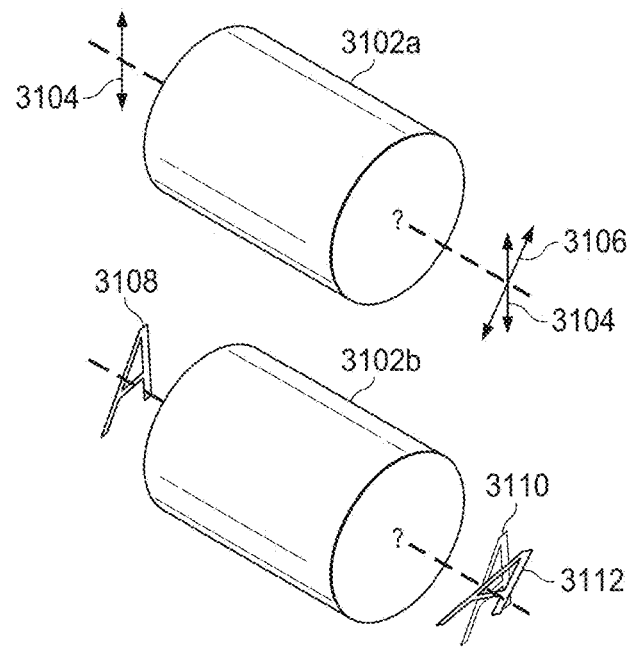
FIG. 31 illustrates the effect of sample concentrations upon the spin angular polarization and orbital angular polarization of a light beam passing through a sample.

FIG. 31 illustrates the difference in impact between spin angular polarization and orbital angular polarization due to passing of a beam of light through a sample 3102. In sample 3102a, there is illustrated the manner in which spin angular polarization is altered responsive to a beam passing through the sample 3102a. The polarization of a wave having a particular spin angular momentum 3104 passing through the sample 3102a will rotate from a position 3104 to a new position 3106. The rotation occurs within the same plane of polarization. In a similar manner, as illustrated with respect to sample 3102b, an image appears as illustrated generally at 3108 before it passes through the sample 3102b. Upon passing the image through the sample 3102b the image will rotate from the position illustrated at 3110 to a rotated position illustrated at 3112. The amount of rotation is dependent upon the level of concentration of the material being detected within the sample 3102. Thus, as can be seen with respect to the sample 3102 of FIG. 31, both the spin angular polarization and the orbital angular momentum will change based upon the concentration of materials within the sample 3102. By measuring the amount of rotation of the image caused by the change in orbital angular momentum, the concentration of a particular material may be determined.

Figure 32:
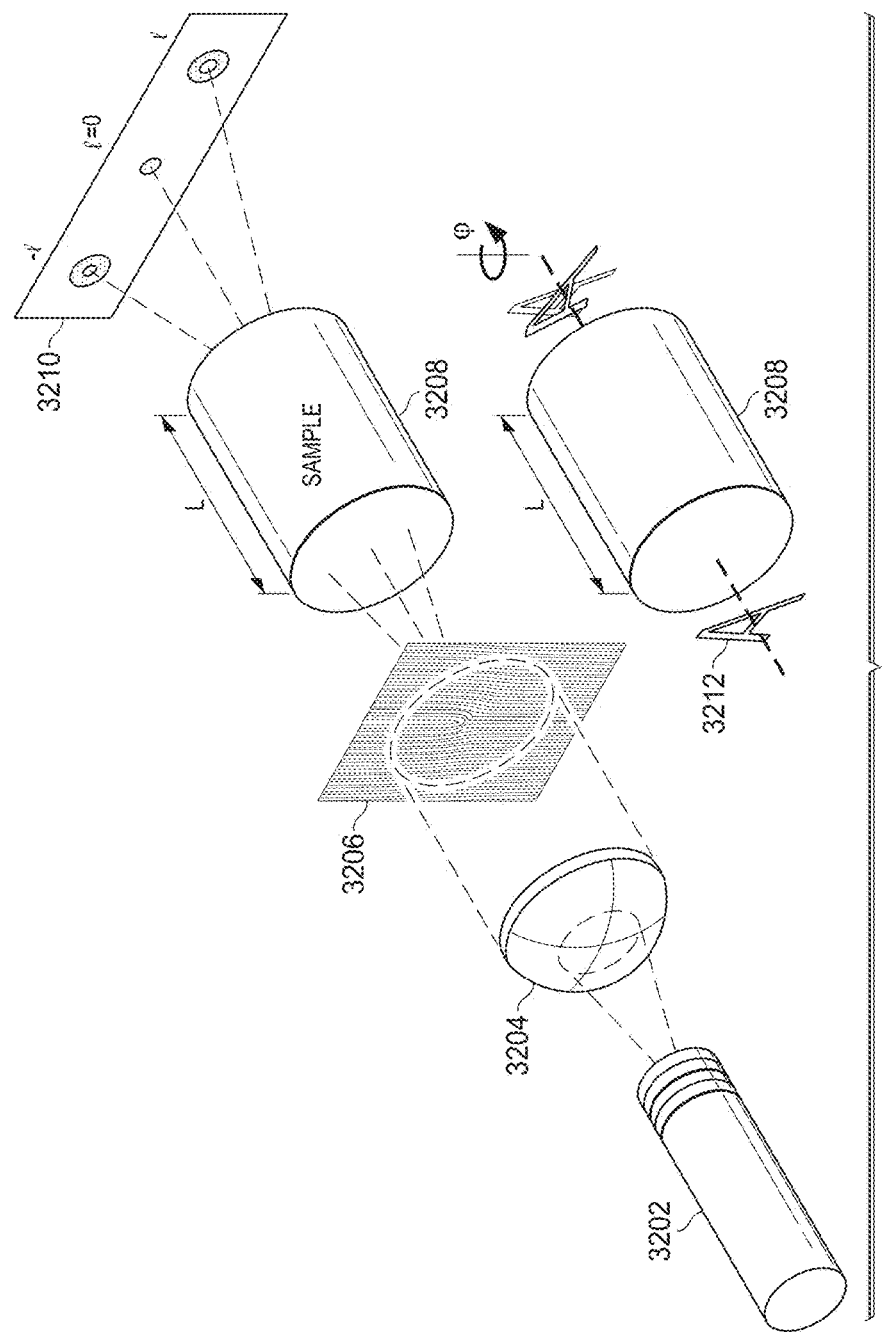
FIG. 32 more particularly illustrates the process that alters the orbital angular momentum polarization of a light beam passing through a sample.

This overall process can be more particularly illustrated in FIG. 32. A light source 3202 shines a light beam through expanding optics 3204. The expanded light beam is applied through a metalab generated hologram 3206 that imparts an orbital angular momentum to the beam. The twisted beam from the hologram 3206 is shined through a sample 3208 having a particular length L. This causes the generation of a twisted beam on the output side of the sample 3208 to create a number of detectable waves having various orbital angular momentums 3210 associated therewith. The image 3212 associated with the light beam that is applied to sample 3208 will rotate an angle φ depending upon the concentration of the material within the sample 3208. The rotation φ of the image 3212 is different for each value orbital angular momentum −1 or +1. The change in rotation of the image Δφ may be described according to the equation:

$$\Delta\varphi = \varphi_l - \varphi_{-l} = f(l, L, C)$$

Where l is orbital angular momentum number, L is the path length of the sample and C is the concentration of the material being detected.

Thus, since the length of the sample L is known and the orbital angular momentum may be determined using the process described herein, these two pieces of information may be able to calculate a concentration of the material within the provided sample.

Figure 33:
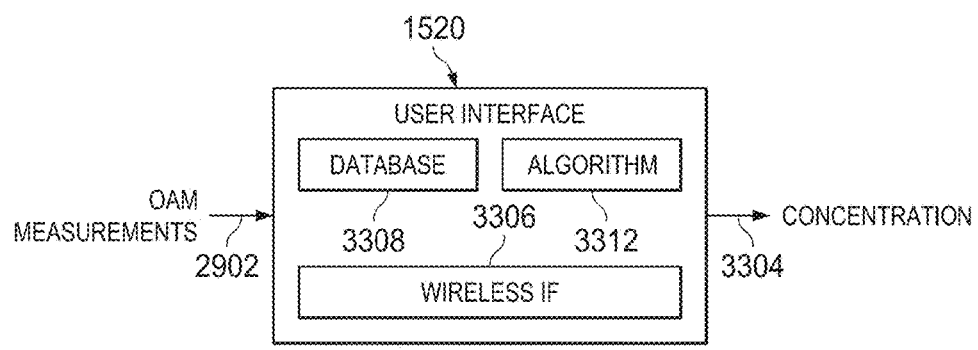
FIG. 33 provides a block diagram of a user interface of the system of FIG. 15.

The above equation may be utilized within the user interface more particularly illustrated in FIG. 33. The user interface 1520 processes the OAM measurements 3302 using an internal algorithm 3302 that provides for the generation of concentration information 3304 that may be displayed in some type of user display. The algorithm would in one embodiment utilize that equation described herein above in order to determine the concentration based upon the length of a sample and the detected variation in orbital angular momentum. The process for calculating the concentration may be done in a laboratory setting where the information is transmitted wirelessly to the lab or the user interface can be associated with a wearable device connected to a meter or cell phone running an application on the cell phone connected via a local area network or wide area network to a personal or public cloud. The user interface 3320 of the device can either have a wired or wireless connection utilizing Bluetooth, ZigBee or other wireless protocols.

Figure 34:
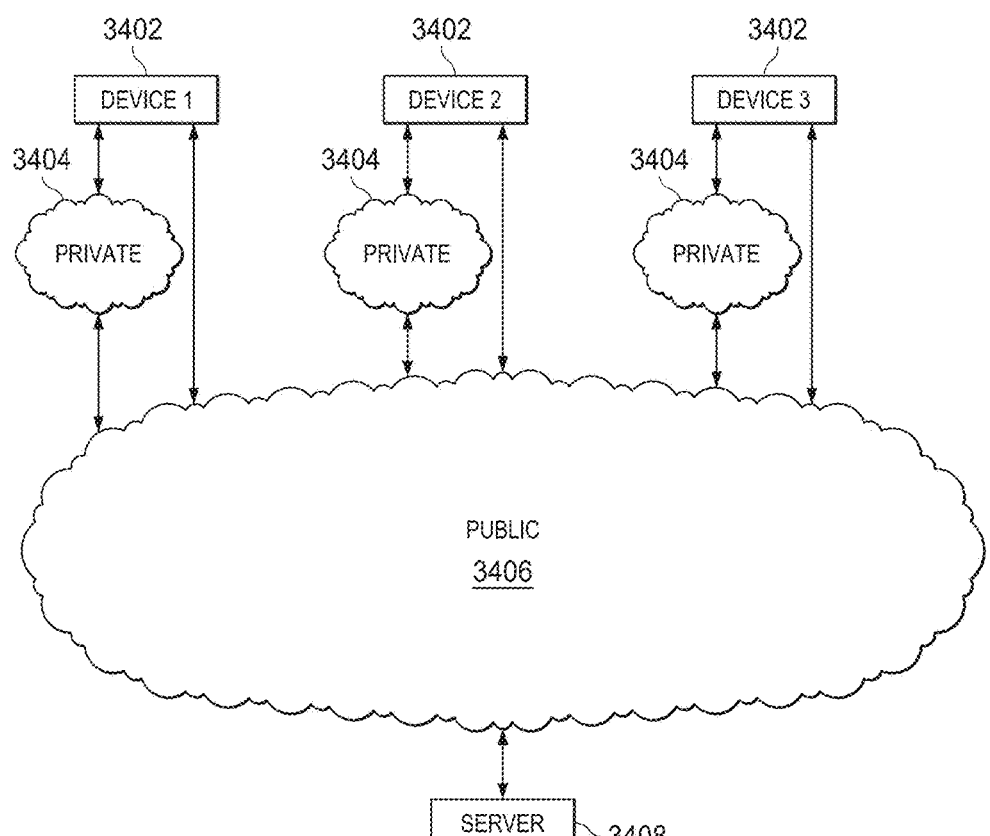
FIG. 34 illustrates a network configuration for passing around data collected via devices such as that illustrated in FIG. 15.

Referring now to FIG. 34, there is illustrated the manner in which the various data accumulated within the user interface 1520 that has been collected in the manner described herein above may be stored and utilized for higher level analysis. Various devices 3402 for collecting data as described herein above may communicate via private network clouds 3404 or with a public cloud 3406. When communicating with a private cloud 3404, the devices 3402 merely store information that is associated with a particular user device that is for use with respect to analysis of the user associated with that user device. Thus, an individual user could be monitoring and storing information with respect to their present glucose concentrations in order to monitor and maintain their diabetes.

Alternatively, when information is compiled from multiple devices 3402 within the public cloud 3406, this information may be provided directly to the public cloud 3406 from the individual devices 3402 or through the private clouds 3404 of the associated network devices 3402. Utilizing this information within the public cloud 3406 large databases may be established within servers 3408 associated with the public cloud 3406 to enable large scale analysis of various health related issues associated with the information processed from each of the individual devices 3402. This information may be used for analyzing public health issues.

Thus, the user interface 1520 in addition to including the algorithm 3302 for determining concentration information 3304 will include a wireless interface 3306 enabling the collected information to be wirelessly transmitted over the public or private cloud as described with respect to FIG. 34. Alternatively, the user interface may comprise a storage database 3308 enabling the collected information to be locally stored rather than transmitted wirelessly to a remote location.

Figure 35:
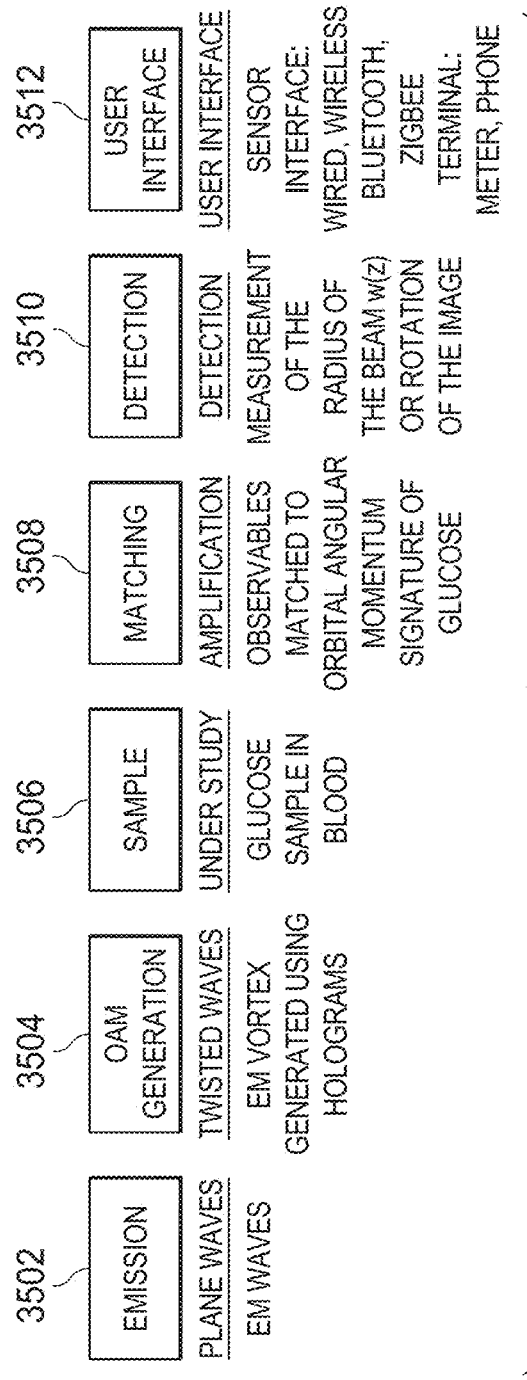
FIG. 35 provides a block diagram of a more particular embodiment of an apparatus for measuring the concentration of glucose using orbital angular momentum.

Referring now to FIG. 35, there is illustrated a particular example of a block diagram of a particular apparatus for measuring the concentration of glucose using the orbital angular momentum of photons of a light beam shined through a glucose sample. The process creates a second-order harmonic with helical light beam using a non-linear crystal such as that described with respect to FIG. 25. The emission module 2402 generates plane electromagnetic waves that are provided to an OAM generation module 3504. The OAM generation module 3504 generates light waves having an orbital angular momentum applied thereto using holograms to create a wave having an electromagnetic vortex. The OAM twisted waves are applied to the sample 3506 that is under study in order to detect the glucose concentration within a sample of blood. A rotated signature exits the sample 3506 in the manner described previously with respect to FIGS. 31-32 and is provided to the matching module 3508. The matching module 3508 will amplify the orbital angular momentum such that the observed concentrations may be calculated from the orbital momentum of the signature of the glucose. These amplified signals are provided to detection module 3510 which measures the radius of the beam w(z) or the rotation of the image provided to the sample via the light beam. This detected information is provided to the user interface that includes a sensor interface wired or wireless Bluetooth or ZigBee connection to enable the provision of the material to a reading meter or a user phone for the display of concentration information with respect to the sample.

In this manner concentrations of various types of material as describe herein may be determined utilizing the orbital angular momentum signatures of the samples under study and the detection of these materials or their concentrations within the sample determine as described.

Figure 36:
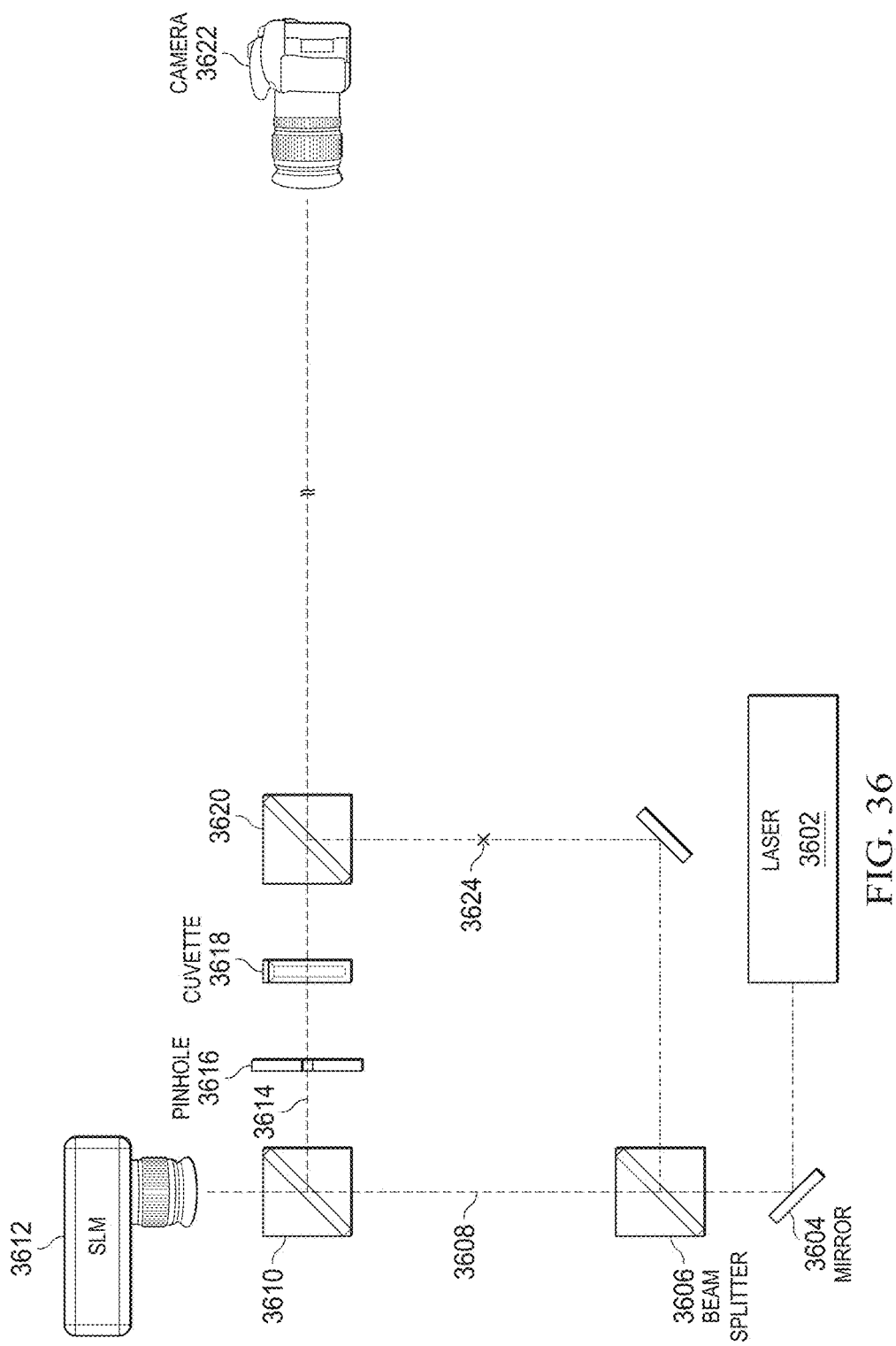
FIG. 36 illustrates a process for testing amyloid-beta concentrations.

As described above, the early onset of Alzheimer's may be determined by detecting concentrations of amyloid-beta in the eye of a patient using the concentration detection techniques described herein above. One process for testing amyloid-beta concentrations is illustrated in FIG. 36. A laser 3602 generates a beam that is reflected off of a mirror 3604. In one embodiment, the light beam generated by laser 3602 has a wavelength of a 538 nm. The reflected beam is passed through a beam splitter 3606. A first beam 3608 interacts at a second beam splitter 3610 with a hologram provided by the spatial light modulator 3612. The spatial light modulator 3612 provides holograms for imparting OAM modes to a light beam from l=−6 to 6. The OAM twisted beam 3614 from the beam splitter 3610 then passes through a pinhole aperture 3616. The pinhole aperture 3616 concentrates the beam to a defined area so that the energy is totally incident on the sample or cuvette. The OAM twisted beam 3614 passes through a cuvette 3618 that holds the amyloid-beta sample. The concentration twisted beam from the cuvette 3618 is split at a beam splitter 3620. A first beam may be imaged by a camera 3622 capturing the intensity of the OAM mode image. A second beam having OAM twisted waves from the beam splitter 3620 is interfered with at 3624 with the original beam including only plane waves from laser 3602 that is reflected by a mirror 3624 from blame splitter 3606. This enables a determination of the helicity and phase of the beam passing through the sample.

Figure 37:
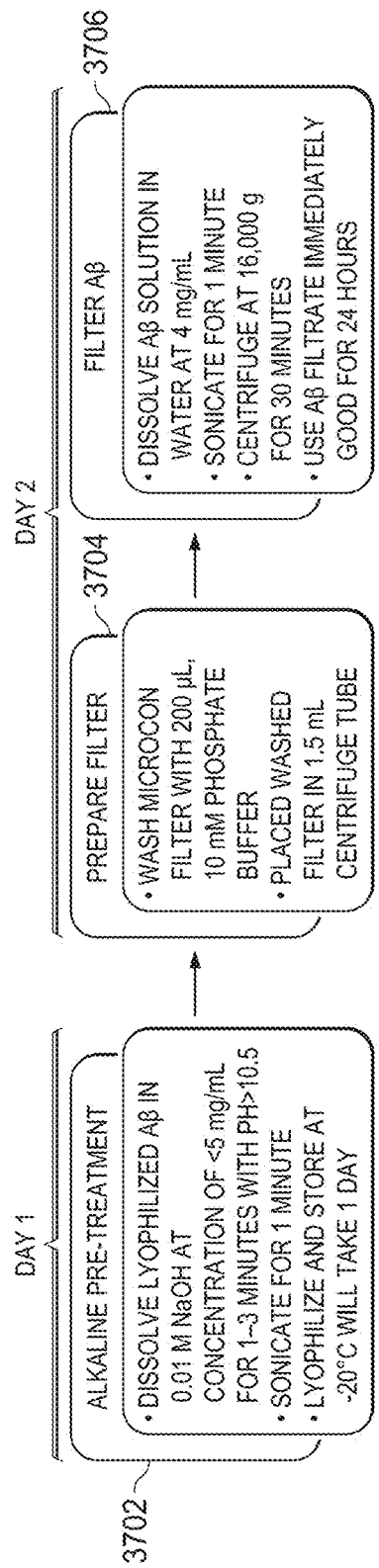
FIG. 37 illustrates an amyloid-beta preparation process.
Figure 43:
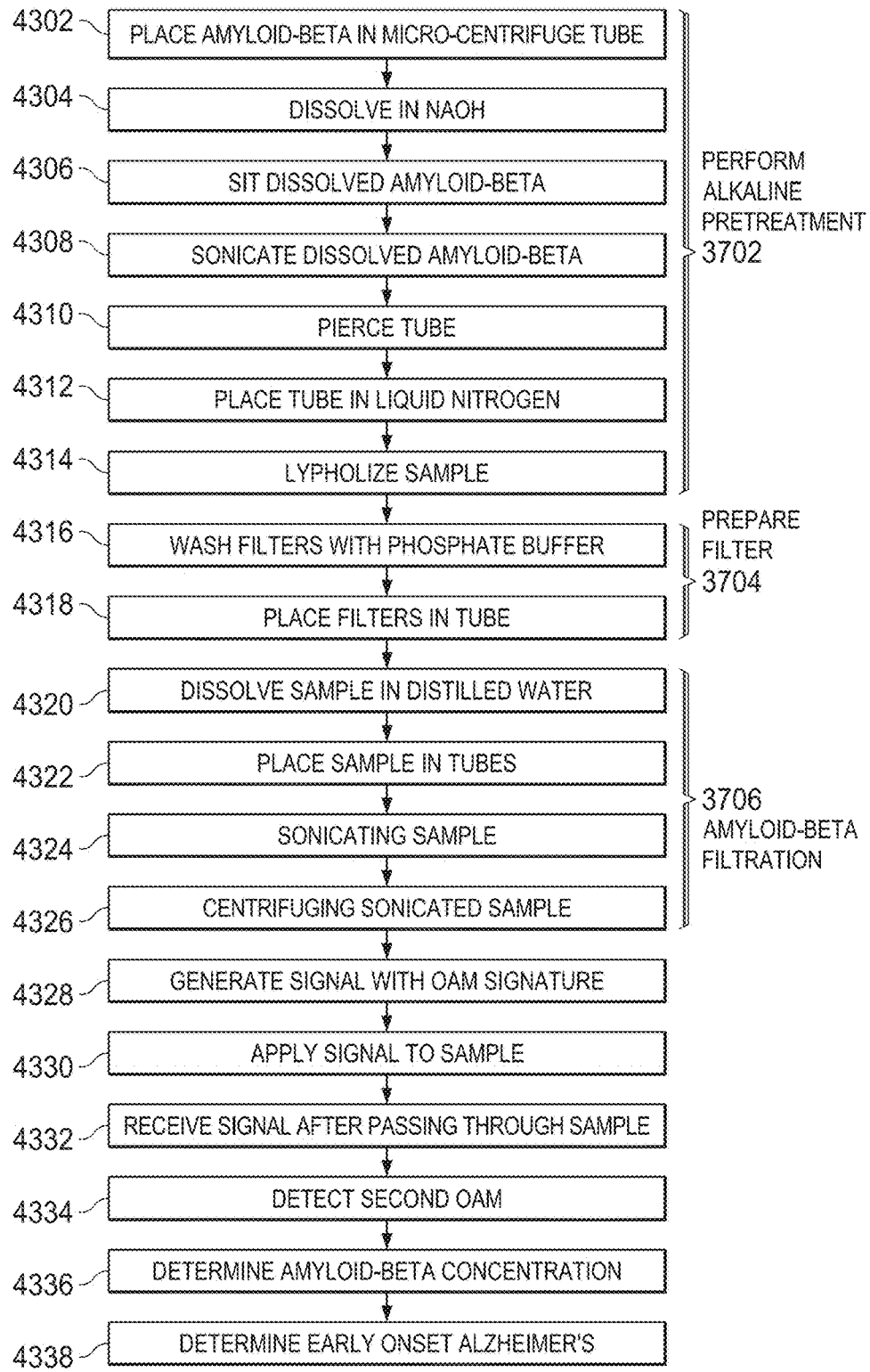
FIG. 43 illustrates a flow diagram of a method of detecting amyloid-beta concentration.

The detection of concentrations of amyloid-beta within a sample in the cuvette requires testing of pre-prepared amyloid-beta concentrations that may be tested in order to determine the amount of change imparted to an intensity OAM mode image by selected concentration values of amyloid-beta. The preparation process for amyloid-beta concentrations is a time-consuming and expensive process. As illustrated in FIG. 37 and FIG. 43, the amyloide-beta preparation requires a two day process. The day one process involves an alkaline pretreatment 3702 of the amyloid beta sample, the preparation of a filter 3704 and filtering of the amyloid beta material 3706 using the filter. The alkaline pretreatment process 3702 involves placing (step 4302) of 0.7 mg of amyloid beta into a 1.5 ml micro-centrifuge tube. The mass of the amyloid-beta is determined using a balance with 100 μg resolution. The amyloid-beta is dissolved (step 4304) with 0.14 ml of 0.01 M NaOH. This mixture is allowed to sit for three minutes (step 4306). The sample is sonicated (step 4308) for one minute in a Branson 1800 Sonicator. A hole is poked into the micro-centrifuge tube (step 4310), and the tube is placed into liquid nitrogen (step 4312). The pierced micro-centrifuge tube is next placed into a larger 50 ml tube and placed into a lyophilizer (step 4314). The 50 ml tube is removed from the lyophilizer 24 hours later. The 1.5 ml micro-centrifuge tube with amyloid beta may be placed into a freezer at −20 degrees centigrade.

The day two preparations begin with the preparation of the filter at step 3704. Two Millipore micro-con centrifugal filters are washed (step 4316) with 200 μl of 10 mM phosphate buffer. The filters are placed inside two 1.5 ml micro-centrifuge tubes (step 4318). To begin the process of amyloid beta filtration 3706, the lyophilized amyloid beta is dissolved into 3 ml of distilled water (step 4320) and 1.5 ml of the amyloid beta solution is placed into each centrifugal filter. The samples are again sonicated (step 4324) for one minute using the Branson 1800 Sonicator. The 1.5 ml centrifuge tubes are placed at opposite ends in the centrifuge and centrifuged at 16,000 g for thirty minutes (step 4326). The filtered amyloid beta will be within the filter and the water will be at the bottom of the centrifuge tube. The amyloid beta filtrate may be used immediately for a period of up to 24 hours. After this time period the amyloid beta filtrate is no longer good. A first signal is generated (step 4328) having an orbital angular momentum signature applied thereto. The first signal is applied (step 4330) to the amyloid-beta test sample. The first signal is received (step 4332) after it passes through the amyloid-beta test sample. A second orbital angular momentum signature is detected (step 4334) within the received first signal. The concentration of amyloid-beta within the amyloid-beta test sample is determined (step 4336) based on a detected second orbital angular momentum signature within the first signal received from the amyloid-beta test sample and determines (step 4338) if the concentration of amyloid-beta provides an indication of an early onset of Alzheimer's.

Figure 38:
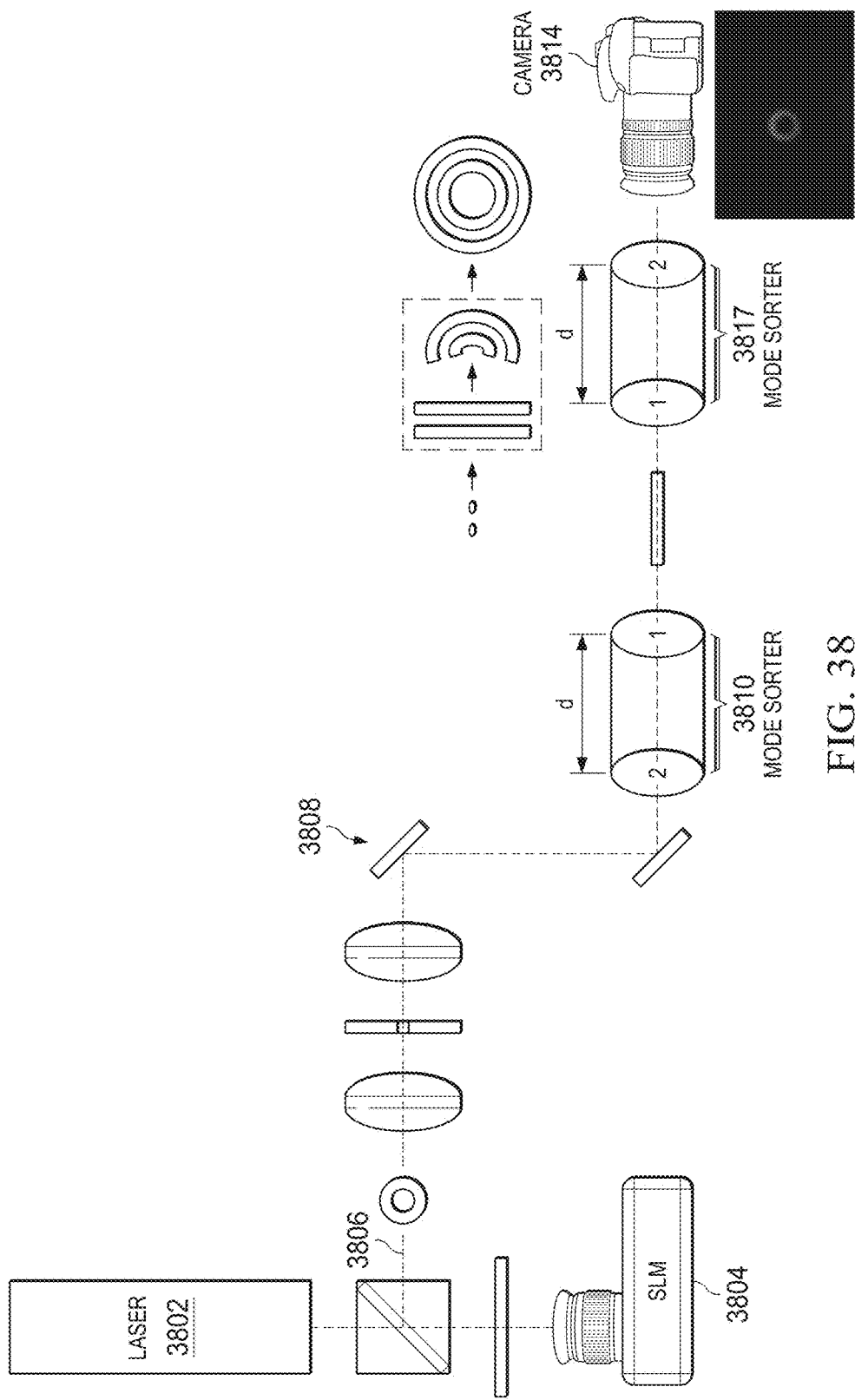
FIG. 38 illustrates an example of a light beam that is altered by a hologram to produce an OAM twisted beam.

It is been noted that the eccentricities of the intensity images produced by shining orthogonal function processed beam through a amyloid-beta sample can have variances due to a number of differing factors. FIG. 38 illustrates an example wherein a light beam produced by a laser 3802 is altered by a hologram provided by an SLM 3804 to generate an OAM twisted beam 3806. The OAM twisted beam in addition to being altered by OAM functions may also be processed using Hermite Gaussian functions, Laguerre Gaussian functions or any other type of orthogonal function. The OAM twisted beam is focused through a system 3808 of lenses and mirrors to direct the beam through a mode sorter 3810. The beam is separated into its different modes when regenerated at mode sorter 3812 and the intensity images may be registered by a camera 3814.

Figure 39:
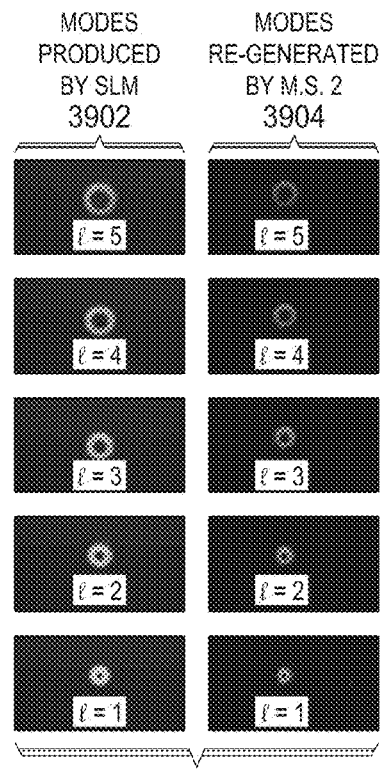
FIG. 39 illustrates various OAM modes produced by a spatial light modulator.

The beam from the laser 3802 has an inherent eccentricity of approximately 0.15. As illustrated in FIG. 39, there are illustrated various OAM modes produced by the SLM in column 3902 for l=5,4,3,2,1. As can be seen, there are differences between the eccentricity of the modes produced by the SLM, and the eccentricity of the modes regenerated by the second mode sorter 3812.

Figure 40:
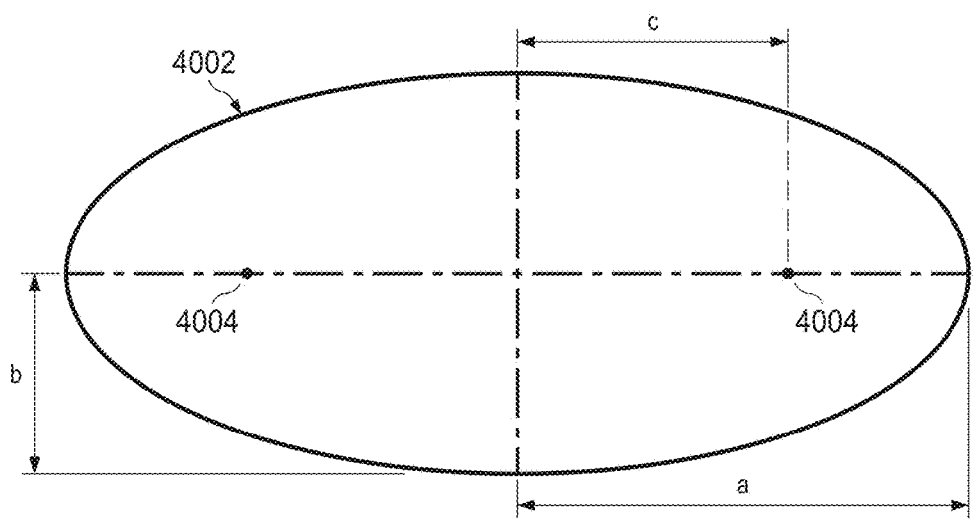
FIG. 40 illustrates an ellipse.

Measurements of eccentricity are performed using Photoshop and Matlab to identify the specific signatures. Referring now to FIG. 40, there is illustrated an example of an ellipse 4002 having a radius "a" along its long axis, a radius "b" along a short axis and a distance "c" to the foci 4004 of the ellipse. The eccentricity of the ellipse is represented by the equation eccentricity=c/a. The eccentricity varies from 0 to 1 with 0 representing a circle and 1 representing a line. The eccentricity equation is calculated according to the following equations:

$$U_{xx} = \frac{1}{N}\sum_{i=1}^{N} x_i^2 + \frac{1}{12}$$

$$U_{yy} = \frac{1}{N}\sum_{i=1}^{N} y_i^2 + \frac{1}{12}$$

$$U_{xy} = \frac{1}{N}\sum_{i=1}^{N} y_i x_i$$

$$common = \sqrt{(U_{xx} - U_{yy})^2 + 4U_{xy}^2}$$

$$2a = 2\sqrt{2}\sqrt{U_{xx}U_{yy} + common}$$

$$2b = 2\sqrt{2}\sqrt{U_{xx}U_{yy} - common}$$

$$c = \sqrt{a^2 - b^2}$$

$$\text{Eccentricity} = \frac{c}{a}$$

where $x_i$ is the x location of the pixels in the ellipse; $y_i$ is the y locations of the pixels in the ellipse; and N is the number of pixels in the ellipse.

It is been found that the eccentricity is greater than 0 when no amyloid-beta sample is present within the cuvette. A number of factors contribute to the nonzero eccentricity. OAM twisted signals have been found to provide different eccentricities based upon a number of different factors that may affect the index of refraction. These factors include things such as the sample distribution of the amyloid-beta within the cuvette due to gravity, the distance of the camera from the spatial light modulator and the camera angle of the camera from the spatial light modulator. Other factors affecting the eccentricity are the cuvette positioning, the index of refraction changes do to the sample, the cuvette shape and the beam incidence and exit angle from the cuvette.

Several image processing factors have also been determined not to cause changes that are outside the margin of error. Changes based on software processing errors, a circular mask that is not OAM, the amyloid-beta sitting time or the amyloid-beta interaction with the glass or plastic comprising the sample container may provide eccentricity changes, but the changes are not due to optical impairments caused by the cuvette orientation, camera alignment, ect. These factors do produce some changes in eccentricity, but they are within the margin of error and the majority of the eccentricity change is based on the signature of the molecule being detected.

Figure 41:
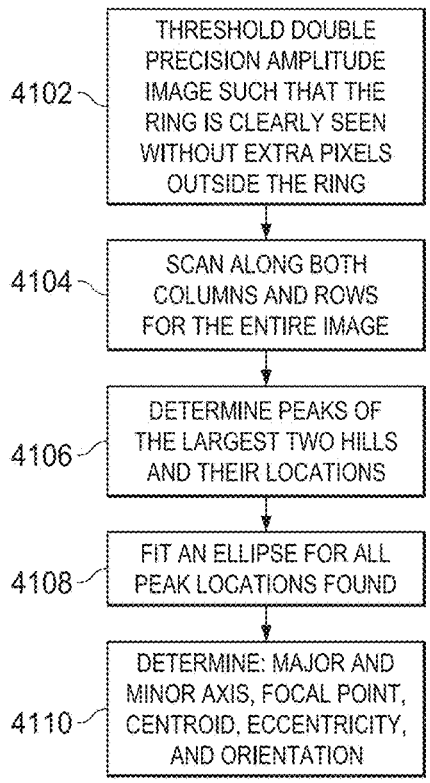
FIG. 41 is a flow diagram illustrating a process for analyzing intensity images.

Referring now to FIG. 41, there is illustrated a flow diagram for analyzing intensity images taken by the camera 3814. The intensity image has applied thereto threshold double precision amplitude to enable the ring to be clearly seen without extra pixels outside of the ring at step 4102. Next at step 4101, both columns and rows are scanned along for the entire image. The peaks of the two largest hills and their locations are determined at step 4106. An ellipse is fit at step 4008 for all peak locations found. Finally, at step 4110, a determination is made of the major and minor axis of the ellipse, the focal point of the ellipse, the centroid, eccentricity and orientation of the ellipse.

Figure 42:
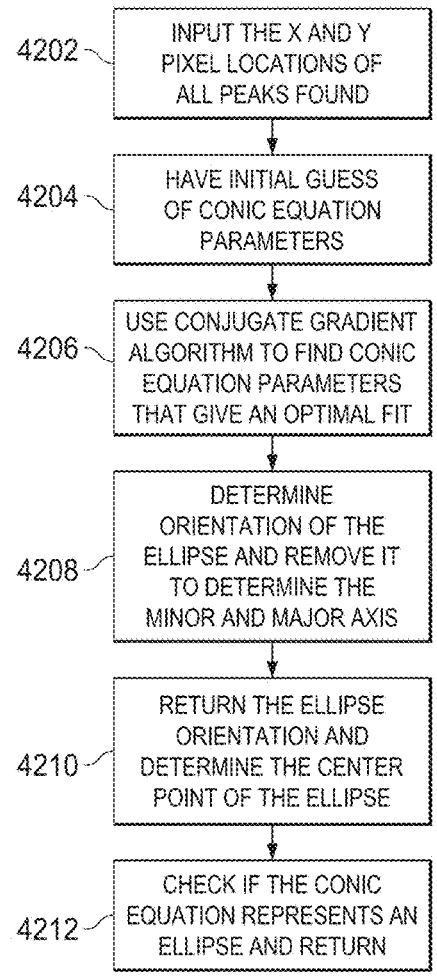
FIG. 42 illustrates an ellipse fitting algorithm.

FIG. 42 illustrates an ellipse fitting algorithm flowchart. The X and Y pixel locations are input at step 4202 for all peaks that are found. An initial guess is provided at step 4204 for the conic equation parameters. The conic equation parameters comprise parameters A, B, C, D and E for the equation $Ax^2+By^2+Cx+Dy+E=0$. The conjugate gradient algorithm is used at step 4206 to find conic equation parameters that provide an optimal fit. An orientation of the ellipse is determined at step 4208 and moved to determine the major and minor axis. The determination of step 4208 is determined according to the equation $$\phi = \frac{1}{2}\tan^{-1}\frac{B}{C-A}$$

The ellipse orientation is returned at step 4210 to determine the central point of the ellipse. Finally, at step 4212, a determination is made if the conic equation represents an ellipse. For an ellipse parameters A and B will exist and have the same sign but will not be equal. Based upon this analysis it is been determined that lateral shift of up to 1 mm can cause significant changes in the measured eccentricity due to clipping of up to 0.2.

It will be appreciated by those skilled in the art having the benefit of this disclosure that this system and method for the early detection of Alzheimer's by detecting amyloid-beta concentrations. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An apparatus for measuring a concentration of amyloid-beta within a chiral solution, comprising:
    signal generation circuitry for generating a first signal having an applied first orbital angular momentum signature and applying the first signal to the chiral solution; and
    a detector for receiving the first signal after the first signal passes through the chiral solution and determining the concentration of amyloid-beta within the chiral solution based on a detected second orbital angular momentum signature caused by the chiral solution, wherein the detected second orbital angular momentum signature comprises an amplitude measurement and a phase measurement.

2. The apparatus of claim 1, wherein the detector negates effects of at least one of sample distribution due to gravity within the chiral solution, angle of camera recording a mode intensity to the chiral solution, a container holding the chiral solution, an angle of incidence of the first signal to the chiral solution and an angle exit of the first signal from the chiral solution to detect the second orbital angular momentum signature.

3. The apparatus of claim 1, wherein the chiral solution is located in an eye of a patient.

4. The apparatus of claim 1, wherein the signal generation circuitry further comprises:
    an emitting source for emitting the first signal comprising a plurality of plane waves; and
    orbital angular momentum generation circuitry for receiving the first signal and applying the first orbital angular momentum signature to the first signal to provide an orbital angular momentum twisted signal.

5. The apparatus of claim 1, wherein the detector further includes circuitry for determining a phase of the first signal after the first signal passes through the chiral solution, wherein the circuitry determines the phase by interfering the first signal having second orbital angular momentum signature therein with the first signal having plane waves therein.

6. The apparatus of claim 1, wherein the signal generation circuitry further comprises a hologram implemented with at least one of an amplitude mask, a phase mask, a spatial light modulator and a digital light processor.

7. The apparatus of claim 1, wherein the detector further comprises:
    an orbital angular momentum detector for determining the detected second orbital angular momentum signature by taking the phase measurement and the amplitude measurement within the first signal from the chiral solution; and
    a processor for determining a concentration of the amyloid-beta within the chiral solution responsive to the detected second orbital angular momentum signature.

8. The apparatus of claim 1, wherein differing signatures indicate different concentrations of the amyloid-beta within the chiral solution.

9. An apparatus for measuring a concentration of amyloid-beta within a chiral solution, comprising:
    an emitting source for emitting a first signal comprising a plurality of plane waves;
    orbital angular momentum generation circuitry for receiving the first signal and applying an orbital angular momentum signature to the first signal to provide an orbital angular momentum twisted signal;
    a transmitter for applying the orbital angular momentum twisted signal to the chiral solution; and
    a detector for receiving the orbital angular momentum twisted signal after the orbital angular momentum twisted signal passes through the chiral solution and determining the concentration of amyloid-beta within the chiral solution based on a detected second orbital angular momentum signature received caused by the chiral solution, wherein the detected second orbital angular momentum signature comprises an amplitude measurement and a phase measurement, wherein the detector further comprises:
        an orbital angular momentum detector for determining the detected second orbital angular momentum signature by taking the phase measurement and the amplitude measurement within the first signal from the chiral solution; and
        a processor for determining a concentration of the amyloid-beta within the chiral solution responsive to the detected second orbital angular momentum signature.

10. The apparatus of claim 9, wherein the detector negates effects of at least one of sample distribution due to gravity within the chiral solution, angle of camera recording a mode intensity to the chiral solution, a container holding the chiral solution, an angle of incidence of the first signal to the chiral solution and an angle exit of the first signal from the chiral solution to detect second orbital angular momentum signature.

11. The apparatus of claim 9, wherein the chiral solution is located in an eye of a patient.

12. The apparatus of claim 9, wherein the detector further includes circuitry for determining a phase of the first signal after the first signal passes through the chiral solution, wherein the circuitry determines the phase measurement by interfering the first signal having the second orbital angular momentum signature therein with the first signal having the plane waves therein.

13. The apparatus of claim 9, wherein the orbital angular momentum generation circuitry further comprises a hologram implemented with at least one of an amplitude mask, a phase mask, a spatial light modulator and a digital light processor.

14. The apparatus of claim 9, wherein differing signatures indicate different concentrations of the amyloid-beta within the chiral solution.

15. A method for detection an early onset of Alzheimer's based upon amyloid beta concentration, comprising:
    generating a first signal having an orbital angular momentum signature applied thereto;
    applying the first signal to a chiral solution;
    receiving the first signal after it passes through the chiral solution;
    detecting a second orbital angular momentum signature within the received first signal, wherein the second orbital angular momentum signature comprises an amplitude measurement and a phase measurement;
    determining a concentration of amyloid-beta within the chiral solution based on a detected second orbital angular momentum signature comprised of the amplitude measurement and the phase measurement within the first signal received from the chiral solution; and
    determining if the concentration of amyloid-beta provides an indication of an early onset of Alzheimers.

16. The method of claim 15, wherein detecting further comprises negating effects of at least one of sample distribution due to gravity within the chiral solution, angle of camera recording a mode intensity to the chiral solution, a container holding the chiral solution, an angle of incidence of the first signal to the chiral solution and an angle exit of the first signal from the chiral solution to detect a change in an eccentricity of the mode intensity.

17. The method of claim 15, wherein the step of applying further comprises the step of applying the first signal to an eye of a patient in a non-intrusive manner.

18. The method of claim 15, wherein generating further comprises:
    emitting the first signal comprising a plurality of plane waves; and
    receiving the first signal; and
    applying the orbital angular momentum signature to the first signal to provide an orbital angular momentum twisted signal.

19. The method of claim 15, wherein the determining the concentration further comprises:
    interfering the first signal having the second orbital angular momentum signature therein with the first signal having plane waves therein; and
    determining a phase of the first signal after the first signal passes through the chiral solution from the interfered first signal.

20. The method of claim 15, wherein the detecting further comprises determining the detected second orbital angular momentum signature by taking the phase measurement and the amplitude measurement within the first signal from the chiral solution.

* * * * *